(12) United States Patent
Kunimoto et al.

(10) Patent No.: US 6,673,223 B2
(45) Date of Patent: Jan. 6, 2004

(54) GAS SENSING AND OXYGEN PUMPING DEVICE, AND APPARATUS USING THE SAME

(75) Inventors: Akira Kunimoto, Kumagaya (JP); Yongtie Yan, Kumagaya (JP); Takashi Ono, Kumagaya (JP)

(73) Assignee: Kabushiki Kaisha Riken, Tokyo (JP)

( * ) Notice: Subject to any disclaimer, the term of this patent is extended or adjusted under 35 U.S.C. 154(b) by 0 days.

(21) Appl. No.: 09/991,744

(22) Filed: Nov. 26, 2001

(65) Prior Publication Data

US 2002/0108856 A1 Aug. 15, 2002

(30) Foreign Application Priority Data

| Nov. 27, 2000 | (JP) | 2000-359040 |
| Nov. 27, 2000 | (JP) | 2000-359041 |
| Dec. 26, 2000 | (JP) | 2000-395673 |
| Feb. 9, 2001 | (JP) | 2001-033330 |

(51) Int. Cl.⁷ .............................................. G01N 27/26
(52) U.S. Cl. ................. 204/426; 204/425; 204/427; 204/290.1; 204/290.14; 204/292; 204/293; 205/781
(58) Field of Search ........................... 204/421–429

(56) References Cited

U.S. PATENT DOCUMENTS

| 3,776,831 A | * | 12/1973 | Roy et al. |
| 3,843,400 A | * | 10/1974 | Radford et al. |
| 4,152,234 A | * | 5/1979 | Pollner |
| 4,224,113 A | * | 9/1980 | Kimura et al. |
| 4,257,863 A | * | 3/1981 | Hoffman |
| 5,393,397 A | * | 2/1995 | Fukaya et al. |
| 5,520,789 A | * | 5/1996 | Takahashi et al. |
| 6,143,165 A | * | 11/2000 | Kurosawa et al. |
| 6,303,011 B1 | | 10/2001 | Gao et al. ................. 204/425 |

FOREIGN PATENT DOCUMENTS

| JP | 9-274011 A | 10/1997 |
| JP | 11-72476 A | 3/1999 |

OTHER PUBLICATIONS

Nakanouchi, Y. et al.; "New Type of Nox Sensors for Automobiles"; *SAE*; No. 961130, pp. 11–18.

* cited by examiner

*Primary Examiner*—T. Tung
(74) *Attorney, Agent, or Firm*—Kubovcik & Kubovcik

(57) ABSTRACT

The present invention discloses a gas sensing device, an oxygen pumping cell, and a gas detection apparatus using the same for detecting lower ranges of gas concentration with high accuracy and stability. An under layer made of oxygen-ion-conductive solid electrolyte was formed between an electrolyte substrate and a sensing electrode, a conversion electrode or a gas treatment electrode. This allows the physical and chemical adhesion between these electrodes and the electrolyte substrate, thereby improving the sensing properties and stability.

9 Claims, 19 Drawing Sheets

GAS SENSING AND OXYGEN PUMPING DEVICE, AND APPARATUS USING THE SAME

BACKGROUND OF THE INVENTION

1. Field of the Invention

The invention relates to a gas sensing (detection) device for detecting the concentration of a gas to be detected, an electrochemical oxygen pumping cell for electrochemically oxidizing or reducing a gas to be processed existing in the atmosphere, and a gas sensor using the same. In particular, the invention relates to a gas sensing device and an oxygen pumping cell to be used in a NOx sensor which can directly measure the concentration of NOx (nitrogen oxides) in automotive or other combustion exhaust.

2. Description of the Related Art

It has been widely demanded to measure automotive exhaust for certain gases, such as HC (hydrocarbon gas), CO (carbon monoxide), and NOx, independent of the presence of other gases. To meet such a demand, gas sensors having high gas selectivities to certain gases alone have been actively proposed in recent years.

As shown in Japanese Patent Laid-Open Publication No. Hei 9-274011, the present inventors have already proposed a mixed potential type NOx sensor of high temperature operation model that uses a zirconia solid electrolyte which is an oxygen ion conductor.

This NOx sensor has a structure in which a collector made of a precious metal such as Pt, and a NOx sensing electrode are formed on a zirconia solid electrolyte substrate, and a reference electrode (or counter electrode) is formed on the zirconia solid electrolyte at the opposite side or the same side of this sensing electrode. In this NOx sensor, a potential difference between the sensing electrode and the reference electrode can be measured to detect the concentration of NOx in the gas to be measured.

The mixed potential type NOx sensor requires that two reactions given by the following equations (1) and (2) occur on the sensing electrode at the same time. In $NO_2$ gas detection, in contrast, reactions given by the equations (3) and (4) need to occur simultaneously. This means that NO gas detection and $NO_2$ gas detection produce sensor outputs of opposite polarities.

In the case of detecting a total NOx concentration in automotive exhaust, coexisting NO and $NO_2$ cause mutual interference, precluding the detection of the total NOx concentration if nothing is done. In view of this, there has been proposed a total NOx sensor of lamination type which is shown in Japanese Patent Laid-Open Publication No. Hei 9-274011.

$$O_2 + 4e^- \rightarrow 2O^{2-} \quad (1)$$

$$2NO + 2O^{2-} \rightarrow 2NO_2 + 4e^- \quad (2)$$

$$2O^{2-} \rightarrow O_2 + 4e^- \quad (3)$$

$$2NO_2 + 4e^- \rightarrow 2NO + 2O^{2-} \quad (4)$$

Here, an electrochemical oxygen pump is used to introduce oxygen from the air into the gas detection chamber so that reducing gases in the gas to be measured, such as HC and CO, are oxidized and rendered harmless. In addition, NO out of NOx is electrochemically converted into $NO_2$, turning NOx into a single gas $NO_2$. The total NOx concentration is detected from a potential difference based on the mixed potential of the single gas $NO_2$.

The detection performance of such a sensor largely depends on the sensitivity characteristics and stability of the sensing electrode. Among sensing electrodes proposed heretofore are $NiCr_2O_4$ (SAE Paper No. 961130), Pt—Rh alloys, and thermet electrodes that contain zirconia solid electrolytes (Japanese Patent Laid-Open Publication No. Hei 11-72476). Each of these sensing electrodes has high sensitivity, whereas further improvements are required of the stability of the sensitivity. This makes it essential to secure not only the stability of the electrode materials but also the stability of a three-phase interface at which the solid electrolyte, the electrode, and the gas phase contact one another. Conventionally, it has been difficult to control the stability of the three-phase interface particularly when the metal-oxide sensing electrodes are used.

Moreover, variations in the adhesion of conventional sensing electrodes to solid electrolyte substrates have caused large property differences between the sensor devices fabricated. This sometimes caused variations in detection performance and drops in yield, contributing to unstable outputs.

Now, the detection performance of the mixed potential type NOx sensor also depends on the performance of its oxygen pump cell for converting NOx in the atmosphere into a single gas NO or $NO_2$. That is, the higher the efficiency to convert NOx in the gas to be detected into NO or $NO_2$, the higher the concentration range can be detected through the sensor output. Besides, the higher this conversion efficiency is, the more accurate the detection of the low concentration range becomes.

It is obvious that emission regulations become increasingly tighter worldwide in the future. The range of NOx detection in automotive engine's exhaust gas treatment systems and the like will be shifted toward yet lower concentrations. To respond to this tide, improvements are required of the NOx conversion performance and stability of the NOx sensor described above.

To detect the concentration of NOx in exhaust with accuracy, HC, CO and other reducing gases, or interference gases, must be fully oxidized and converted into harmless gases such as $H_2O$ and $CO_2$. Solid-catalytic oxidation and removal are insufficient for this purpose. Then, electrochemical oxidation by using an oxygen pumping cell is required. Accordingly, the performance and stability of the oxygen pumping cell for performing the oxidation of the reducing gases and the like also become important to the mixed potential type sensor.

SUMMARY OF THE INVENTION

As has been described, it is desired of recent gas sensors to measure lower ranges of gas concentrations with high accuracy and stability. It is thus an object of the present invention to improve the electrode performance of gas sensing devices and oxygen pumping cells which has a large influence on the detection performance and stability of gas sensors.

In view of the foregoing object, the present inventors propose that the object be achieved by the following means.

A gas sensing device is provided comprising: an oxygen-ion-conductive solid electrolyte substrate; a sensing electrode active to a gas to be detected and oxygen, arranged on the solid electrolyte substrate; and a reference electrode active to at least oxygen, fixed onto the solid electrolyte substrate. Here, an electrode under (base) layer made of an oxygen-ion-conductive solid electrolyte is arranged between the sensing electrode and the solid electrolyte substrate of the gas sensing device. As a result, the interface between the electrode and the solid electrolyte improves in physical and chemical adhesion. This allows stable gas detection and provides a remedy to such problems as electrode exfoliation and the occurrence of cracks at the time of fabrication.

Moreover, an oxygen pumping cell is provided comprising: an oxygen-ion-conductive solid electrolyte substrate; a first electrode active to at least a gas to be processed and oxygen, arranged on the solid electrolyte substrate; a second electrode active to at least oxygen, arranged on the solid electrolyte substrate; and means for applying a predetermined voltage to between the electrodes. Here, an electrode under layer made of an oxygen-ion-conductive solid electrolyte is arranged at least between the first electrode and the solid electrolyte substrate of the oxygen pumping cell. This also improves the physical and chemical adhesion between the electrode and the solid electrolyte, thereby reducing the interface resistance of the electrode for improved oxygen pumping performance. Furthermore, the electrode interface improves in stability, allowing a significant improvement to the degradation resistance of the sensor output.

DETAILED DESCRIPTION OF THE PREFERRED EMBODIMENTS

Figure 1:
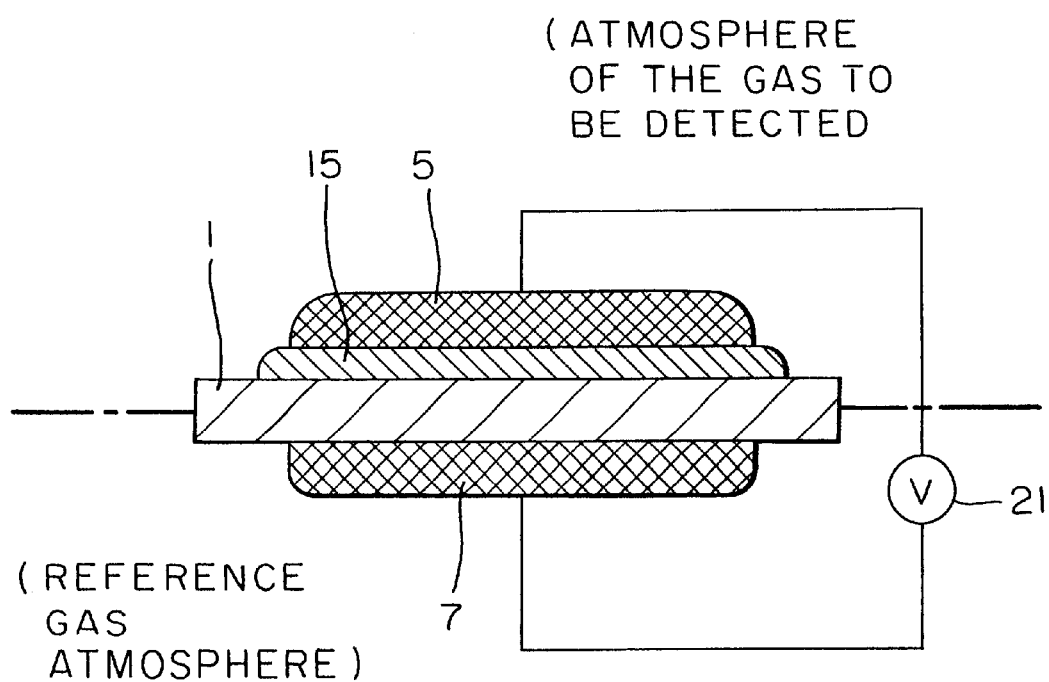
FIG. 1 shows a cross sectional view of an embodiment of the sensing device structure according to the present invention.

Initially, a gas sensing (detection) device of the present invention will be described with reference to FIG. 1. According to the configuration of the sensing device of the present invention shown in FIG. 1, a sensing electrode 5 is fixed to one side of an oxygen-ion-conductive solid electrolyte substrate 1 via an electrode base layer 15 which is made of an oxygen-ion-conductive solid electrolyte. A reference electrode 7 is fixed to the other side of the solid electrolyte substrate 1. A difference in electrode potential between the sensing electrode 5 and the reference electrode 7 is measured by a voltmeter 21. Although not shown in FIG. 1, collectors (conductive leads) of Pt or the like are actually formed on the bottom or top surfaces of the electrodes 5 and 7. Here, at least the sensing electrode 5 needs to be exposed to an atmosphere that contains oxygen of or over 0.1% by volume. For faster gas response, exposure to an atmosphere containing oxygen of or over 1% by volume is preferable.

When the gas to be detected is NOx, the reactions expressed in the foregoing equations (1) and (2), or (3) and (4), occur on the sensing electrode 5 simultaneously, thereby causing an electrode mixed potential. In the configuration of FIG. 1, the reference electrode 7 is opposed to the sensing electrode 5 across the solid electrolyte substrate 1. Unlike the sensing electrode 5, the reference electrode 7 is put under a reference atmosphere which is isolated from the gas to be detected. When the reference electrode 7 is also active to the gas to be detected, the reference electrode 7 can be blocked thus from the atmosphere of the gas to be detected to produce an output. On the other hand, if the reference electrode 7 is made of a material inactive to the gas to be detected, the sensing electrode 5 and the reference electrode 7 may be placed on one side of a solid electrolyte film 1' as shown in FIG. 2, being exposed to the same atmosphere. In this case, the reference electrode 7 must be active to at least oxygen, desirably with oxygen activity equivalent to that of the sensing electrode 5. When both the electrodes are placed on the same side, the electrodes may be arranged on a solid electrolyte film formed over an insulating substrate as shown in FIG. 2. Needless to say, a solid electrolyte substrate may also be used as in FIG. 1.

Here, the solid electrolyte substrate 1 is not particularly limited as long as it has an oxygen ion conductivity. A zirconia solid electrolyte having yttria added as a stabilizer is a favorable material for making the substrate since it is chemically stable and has excellent mechanical strength properties. In this case, yttria of 3–10% by mole, or preferably 5–8% by mole, is added to obtain high substrate strength and ion conductivity. While the solid electrolyte substrate 1 of FIG. 1 is formed as a close-grained plate, it may be porous as long as the reference electrode 7 is inactive to NOx. Here, the solid electrolyte may be made into a film on which each electrode is formed.

The sensing electrode of the present invention must be active to oxygen and the gas to be detected. As employed herein, activity refers to so-called electrode activity, or that the electrode produces predetermined electrode potentials due to oxygen and the gas to be detected. This sensing electrode may be made of a metal oxide or precious metal that is active to the gas to be detected and oxygen.

For NOx detection, the metal oxide favorably contains at least Cr. It is yet preferable that the Cr-containing metal oxide is any one of $NiCr_2O_4$, $FeCr_2O_4$, $MgCr_2O_4$ $Cr_2O_3$, or a mixture thereof. Meanwhile, the precious metal may be any one of NOx- and oxygen-active Rh, Ir, and Au, a mixture containing the same, or an alloy thereof. Pt—Rh alloys are alloys of Pt, which is a second precious metal inactive to NOx and active to oxygen, and Rh, which is the first precious metal active to NOx and oxygen. Pt—Rh alloys have high sensitivity characteristic to NOx, and thus can be used as a precious-metal NOx sensing electrode.

For the sake of improved performance, precious metal may be added to a metal-oxide electrode to make the sensing electrode. For example, in the electrode configuration of the present invention, the first precious metal active to the gas to be detected and oxygen may be added to the metal-oxide sensing electrode 5 mentioned above. With respect to the total weight of the electrode, a first precious metal of 40–70% by weight can be added to suppress firing warpage greatly. This allows a further improvement in the stability of the electrode of the present invention. Besides, adding a precious metal material active to the gas to be detected can avoid a drop in the activity of the entire electrode to the gas to be detected. The amount of this first precious metal to be added favorably falls within the range of 40–60% by weight. When this amount of addition falls below 40% by weight, the electrode easily causes cracks and exfoliation with a greater amount of drift. Above 70% by weight, the electrode suffers a larger drop in sensitivity. In the case of NOx detection, the first precious metal may be Ir, Au, Rh, or a mixture thereof. Some of these precious metal elements may exist in the form of oxides, with the same effect.

In the electrode configuration of the present invention, adding the second precious metal to the above-mentioned metal-oxide sensing electrode 5 as much as 0.05–5% by weight with respect to the total amount of the electrode allows a great reduction in electrode interface resistance. As a result, the electrode of the present invention can be made yet stabler in performance. The amount of this second precious metal to be added preferably falls within the range of 0.05–3% by weight, and yet preferably 0.1–1% by weight, with respect to the total amount of the electrode. When this amount of addition falls below 0.05% by weight, the effect is smaller. When the amount of addition exceeds 5% by weight, the electrode suffers a drop in sensitivity. In the case of NOx detection, this second precious metal material may be Pt, Pd, Ru, or a mixture thereof. Some of these precious metal elements may exist in the form of oxides, which falls within the main scope of the present invention.

Adding both the NOx-and-oxygen-active first precious metal and the NOx-inactive second precious metal to the above-described metal-oxide sensing electrode 5 allows a further improvement in the stability of the electrode of the present invention. Here, the amount of the second precious metal to be added favorably falls within the range of 0.05–2% by weight, and preferably 0.1–1% by weight, with respect to the total weight of the electrode. When this amount of addition falls below 0.05% by weight, no effect will be obtained. Above 2% by weight, the electrode decreases in NOx activity with a drop in sensitivity. When the second precious metal is added, the amount of the first precious metal to be added should fall within the range of 10–70% by weight. This amount of addition favorably falls within the range of 40–70% by weight, and preferably 40–60% by weight. When the amount of the first precious metal to be added falls to or below 10% by weight, the addition of the second precious metal will produce no great effect. At or above 70% by weight, the sensitivity performance may drop.

For NOx detection, the first precious metal, active to NOx and oxygen, is desirably made of one or more types out of Ir, Au, and Rh as described above. The second precious metal, active to oxygen and inactive to NOx, is desirably made of one or more types out of Pt, Pd, and Ru.

An oxygen-ion-conductive solid electrolyte is also desirably added to the sensing electrode of the present invention. This increases the three-phase interface (interface where the electrode, the solid electrolyte, and the oxygen-coexisting gas to be detected exist at the same time), allowing the electrode impedance to be lowered to obtain stabler sensor outputs. Favorable solid electrolytes to be added to the electrode are oxygen-ion-conductive zirconia solid electrolytes. Zirconia solid electrolytes containing any one of magnesia, ceria, scandia, and yttria as a stabilizer are preferable.

The amount of the solid electrolyte to be added should fall within the range of 5–25% by weight, and preferably 10–20% by weight, with respect to the total weight of the electrode. Below 5% by weight, the addition provides no effect. Above 25% by weight, the gas sensitivity drops. The zirconia solid electrolyte to be added to the sensing electrode and the zirconia solid electrolyte to serve as a stabilizer in the electrode base layer to be described layer can be made identical in type to obtain superior sensor output stability.

As described above, the sensing electrode may be made of various metal oxides. Nevertheless, because of being poor in sinterability and generally smaller in sintering shrinkage, these oxides tend to produce distortion against the solid electrolyte substrate. Moreover, since the lamination type NOx sensor to be described later is typically composed of green sheets of solid electrolyte, the sintering warpage becomes greater to facilitate cracks and exfoliation of the electrode. In the present invention, an electrode under layer that also functions as a physically- or chemically-stable junction layer is arranged between the sensing electrode and the solid electrolyte substrate. This makes it possible to control the distortion between the electrode and the solid electrolyte substrate.

The electrode under layer is made of an oxygen-ion-conductive solid electrolyte. Precious metals may be added thereto. As the oxygen-ion-conductive solid electrolyte, zirconia solid electrolytes are preferable in view of electrode stability or cost reduction. Here, the optimum solid electrolyte somewhat varies according to the presence or absence of precious metal additives. The following are descriptions of the respective cases:

1) Electrode Under Layer Containing no Precious Metal

When the electrode under layer contains no precious metal, the (zirconia) solid electrolyte is yttria-free or, if any, restricted to an amount of not more than 3% by mole. That is, for the electrode under layer to have oxygen ion conductivity, the use of a non-yttria stabilizer is essential. For example, yttria contained not as much as 3% by mole, if any, cannot exert sufficient oxygen ion conductivity. This requires another stabilizer to be added at the same time. Since non-yttria stabilizers are generally expensive, yttria is desirably used together in terms of costs.

Among the non-yttria stabilizers available are publicly-known ones including oxides of alkaline-earth metals such as magnesia and calcia, and oxides of rare-earth metals such as ceria (cerium oxide), neodymium oxide, gadolinium oxide, ytterbium oxide, and Scandia (scandium oxide). Of these, magnesia, ceria, and scandia are particularly favorable. An oxygen-ion-conductive zirconia solid electrolyte containing at least one of these can be used as the electrode under layer with a significant improvement in the electrode performance and stability. Besides, the amount of these non-yttria stabilizers to be added to the zirconia solid electrolyte of the electrode base layer can be confined within the range of 3–30% by mole, or preferably 5–20% by mole, for yet stabler performance. When the amount of the stabilizer to be added falls below 3% by mole, the sensor performance drops due to insufficient ion conductivity. Above 30% by mole, the solid electrolyte deteriorates in physical strength properties, lowering the stability of the electrode under layer 15. It is desirable that the added stabilizer be evenly dispersed into the zirconia for complete solid solution. The effect of the present invention will not be affected, however, even if minute amounts of the stabilizers remain in grain boundary or the like in microscopic terms.

As a physical component factor, the voidage of the electrode under layer desirably falls within the range of 5–40%, and preferably 10–30%. Voidages of 5% and lower make it difficult to absorb sintering distortion and thermal-expansion distortion between the electrode film and the solid electrolyte substrate. Voidages of 40% and higher reduce the mechanical film strength as a junction layer, facilitating a drop in stability and film defects during fabrication. In addition, the electrode under layer desirably has a thickness of 3–30 μm, and preferably 5–10 μm. At or below 3 μm, an insufficient mechanical link of the film weakens the effect of the present invention. At or above 30 μm, the electrode under layer itself causes greater film distortion, lowering the adhesion with the sensing electrode.

2) Electrode Under Layer Containing Precious Metal

As in 1), the oxygen-ion-conductive solid electrolyte is preferably made of a zirconia solid electrolyte as an electrode under layer in view of electrode stability or cost reduction. When a precious metal is added to the electrode under layer, yttria can be exclusively used as a stabilizer to be added to the zirconia solid electrolyte. In addition to yttria, ceria, magnesia, and scandia are preferable as stabilizers in terms of performance. The amounts of these stabilizers to be added should fall within the range of 3–20% by mole with respect to the total amount of the solid electrolyte. A range of 5–20% by mole is preferable, and 5–15% by mole is yet preferable. When the amount of the stabilizers to be added falls to or below 3% by mole, the sensor output drops due to insufficient oxygen ion conductivity. When the amount of addition reaches or exceeds 20% by mole, the electrode under layer decreases in film thickness, increasing a drop in stability and variations in output.

The precious metal to be added is divided into two types. That is, first precious metal elements which are active to the gas to be detected and oxygen, and second precious metal elements which are inactive to the gas to be detected and active to oxygen. As mentioned above, on the case of NOx gas detection, the first precious metal elements active to NOx and oxygen are divided into Au, Ir, and Rh. The second precious metal elements inactive to NOx and active to oxygen are divided into Pt, Pd, and Ru. Then, one or more types out of either precious metal elements are added to the electrode under layer 15. Both first and second precious metal elements may be added together.

When the first precious metal is exclusively added to the electrode under layer 15, stable electrode performance can be obtained by confining the amount of addition within the range of 0.1–30% by weight, and preferably 1–20% by weight, with respect to the total amount of the electrode under layer. When the amount of addition falls below 0.1% by weight, no effect will be obtained from the addition. Above 30% by weight, the electrode under layer decreases in ion conductivity with a drop in the sensor output.

On the other hand, when the second precious metal is exclusively added to the electrode under layer 15, stable electrode performance can be obtained by confining the amount of addition within the range of 0.05–4% by weight, and preferably 0.1–2% by weight. When the amount of addition falls below 0.05% by weight, no effect will be obtained. Above 4% by weight, the sensor output drops.

The first and second precious metals mentioned above may be added to the electrode base layer at the same time. In this case, a favorable electrode can be obtained by adding the first precious metal within the range of 0.1–30% by weight, or preferably 1–15% by weight. The amount of the second precious metal to be added favorably falls within the range of 0.05–4% by weight, and preferably 0.1–2% by weight, similar to the case of exclusive addition.

Physical factors of the electrode base layer, such as a voidage and a thickness, desirably fall within the same ranges due to the same reasons as in the foregoing 1) electrode under layer containing no precious metal.

As described above, the provision of the electrode under layer can improve the physical and chemical adhesion between the electrode and the solid electrolyte, reducing the interface resistance of the electrode. This also enhances the stability of the electrode interface, with a significant reduction in the sensor output drift and the like.

Moreover, Al may be added to the solid electrolyte substrate of zirconia which contains yttria as a stabilizer. Here, the amount of Al to be added desirably falls within the range of 0.01–1% of the solid electrolyte substrate by weight. The Al contained in the solid electrolyte can significantly lower the temperature for sintering the solid electrolyte substrate and the electrodes integrally at the same time. This provides a sensing electrode of yet higher activity. It is desirable that Al be evenly dispersed into the solid electrolyte for solid solution.

A voltmeter (circuit) is typically used as the means for measuring the potential difference between the sensing electrode 5 and the reference electrode 7. In such a voltmeter-based method, a certain amount of current is taken out through the electrodes to the measuring system. This requires a considerable input impedance as compared to the impedances of the electrodes, for the sake of accurate sensor output. There is another method that uses no voltmeter as the means for measuring the potential difference. The detection cell and a comparison cell (battery) are connected in parallel, and the comparison cell is measured for a voltage at which the current flowing between the two cells becomes zero. In this method, the sensor electromotive force can be measured without taking any current out of the detection device at all.

For higher ion conductivity, at least the electrodes of the sensing device and the solid electrolyte making contact with the electrodes are heated to a predetermined temperature. In fact, they must be maintained at or above 300–400° C. at which the zirconia solid electrolyte increases in ion conductivity. The heating means may be an external heat source or a self-heating heater that is integrated into the gas sensing device.

The above-described gas sensing device is capable of measurement with NOx gas, HC gas, CO gas, $NH_3$ gas, and the like as the gas to be detected. In particular, the device offers a superior effect when used as a NOx sensor for detecting a total NOx concentration.

Figure 3:
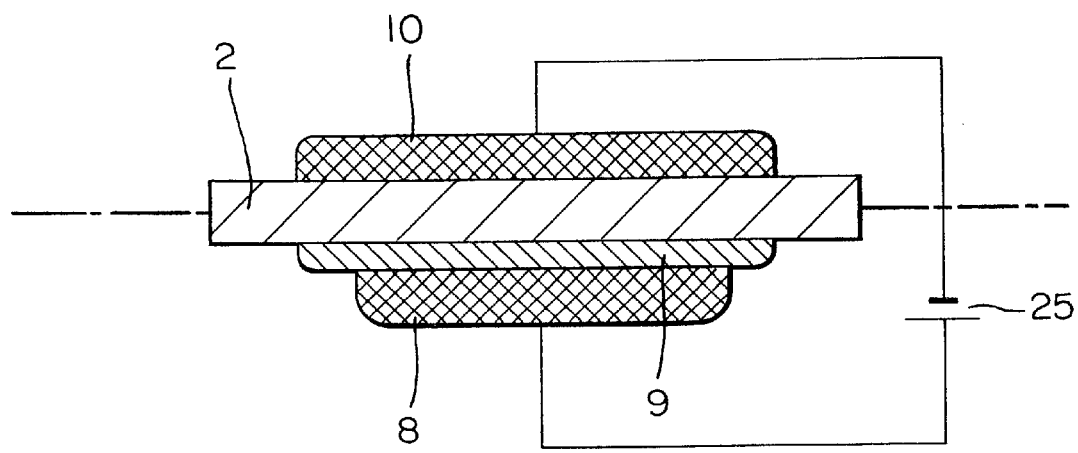
FIG. 3 shows a cross sectional view of an embodiment of the oxygen pumping cell structure according to the present invention.

Now, description will be given of an oxygen pumping cell in the present invention. According to the configuration of the oxygen pumping cell of the present invention shown in FIG. 3, an electrode under layer 9 made of an oxygen-ion-conductive solid electrolyte is formed on an oxygen-ion-conductive solid electrolyte substrate 2. A first electrode 8 is formed on this electrode under layer 9. A second electrode 10 is fixed across the solid electrolyte substrate 2. In FIG. 3, the first electrode 8 and the second electrode 10 are used as an anode electrode and a cathode electrode, respectively. This forms an oxygen pumping cell in which oxygen ion is electrochemically supplied from the second-electrode side. In the diagram, the second electrode is exposed to an atmospheric air. The atmosphere need not contain oxygen gas as long as there exists water ($H_2O$) or oxygenated compound gas such as carbon dioxide ($CO_2$). That is, the second electrode (cathode electrode) constituting the oxygen pumping cell can also electrolyze $H_2O$ or $CO_2$ for oxygen ion supply.

In the oxygen pumping cell according to the present invention, it is essential that an electrode under layer be formed at least under the first electrode which functions as a working electrode for effecting the intended gas conversion. In FIG. 3, the electrode under layer is formed under the first electrode alone, whereas it may also be formed under the second electrode.

Moreover, although not shown in the diagram, lead conductors are preferably formed to apply voltage to the first and second electrodes. On the first electrode, an inorganic porous member may be arranged as an electrode protective film or the like.

The solid electrolyte substrate 2 favorably has the form of a substrate. In some cases, however, a thick solid electrolyte layer may be formed so that the electrode under layer and the first electrode or the second electrode of the present invention is laminated thereon. If the atmosphere on the side to which the first electrode is fixed contains oxygenated compound gas, the second electrode may be arranged on the same side as the first electrode is.

Like the solid electrolyte substrate of the gas sensing device described above, the solid electrolyte substrate 2 of the oxygen pumping cell is also favorably made of a zirconia solid electrolyte having yttria added as a stabilizer, in consideration of costs, chemical stability, and mechanical strength properties. Here, the amount of yttria to be added is confined within the range of 3–10% by mole, or preferably 5–8% by mole.

The first electrode must be active to the gas to be processed and oxygen. For example, in case of a NOx converting pump cell for oxidizing or reducing NOx in the presence of oxygen, it is desirable that the first electrode be composed chiefly of one type out of Ir, Rh, Au, Pt—Rh alloys, Ir—Rh alloys, Pt—Ru alloys, Au—Rh alloys, and Ir—Au alloys which are highly active to NOx and oxygen. This composition ensures favorable performance as a gas converting oxygen pumping cell for oxidizing NO in NOx into $NO_2$ or reducing $NO_2$ into NO.

Take, as another example, an oxygen pumping cell (gas treatment pump cell) by which reducing gases in exhaust, such as HC and CO, are rendered harmless and eliminated in the NOx sensor. Here, the first electrode can be made of any one of Pt, Pd, Ir, Au, and Rh, or an alloy thereof, to ensure favorable performance.

An oxygen-ion-conductive zirconia solid electrolyte is effectively added to make the first electrode porous and increase the electrode activity. This provides stable pump performance. Suitable zirconia solid electrolytes to be added here are ones that contain one or more types out of magnesia, ceria, scandia, and yttria as a stabilizer. A zirconia solid electrolyte containing the same stabilizer as the one in the zirconia solid electrolyte of the electrode base layer to be described later can be added to the first electrode for superior stability.

Adding these solid electrolytes in the ratio of 5–25% by weight, or preferably 5–20% by weight, with respect to the total amount of the first electrode provides an electrode of greatly improved activity and excellent stability. Improvements can also be achieved simply by adding stabilizer-free zirconia or chemically-stable alumina to increase the porosity of the first electrode. In this case, the amount of addition should fall within the range of 5–40% by weight, and preferably 10–30% by weight.

As described above, in the oxygen pumping cell of the present invention, an electrode under layer made of an oxygen-ion-conductive solid electrolyte is arranged at least between the first electrode and the solid electrolyte substrate 2. Like the electrolyte substrate layer applied to the gas sensing device, this electrolyte substrate layer may contain precious metal. Hereinafter, an electrode under layer containing no precious metal and an electrode base layer containing precious metal will be described separately.

1) Electrode Under Layer Containing No Precious Metal

The electrode under layer 9 to be formed on the solid electrolyte substrate 2 is also made of a zirconia solid electrolyte. In the absence of precious metal, stabilizers other than yttria are added. It is desirable that the zirconia solid electrolyte of the electrode base layer be yttria-free, whereas addition of 3% or less by mole causes no practical problem. The yttria content is favorably 2% or less by mole, and preferably 1% or less by mole. The stabilizers other than yttria may be the publicly-known ones mentioned above. In particular, at least one type out of magnesia, ceria, and scandia can be added with a significant improvement in the performance of the oxygen pump cell. This amount of addition desirably falls within the range of 3–30% by mole, and preferably 5–20% by mole, with respect to the total amount of the solid electrolyte.

Accordingly, the physical and chemical adhesion between the electrode and the solid electrolyte can be improved to reduce the interface resistance of the electrode for improved oxygen pumping performance. This also enhances the stability of the electrode interface, allowing a significant reduction in the degradation of the sensor output.

Furthermore, stable performance improvements can be achieved by confining this electrode under layer within voidages of 5–40% by volume and average thicknesses of 3–30 $\mu$m, or by confining the amount of the non-yttria stabilizers to be added to the zirconia solid electrolyte of the electrode base layer within 3–30% by mole.

2) Electrode Under Layer Containing Precious Metal

The electrode under layer 9, when precious metal is added thereto, may be made of a zirconia solid electrolyte that contains yttria alone as a stabilizer. Among other stabilizers, magnesia, ceria, and scandia are particularly desirable. Here, the amount of the stabilizer desirably falls within the range of 3–30% by mole, and preferably 5–20% by mole. When the amount of addition falls to or below 3% by mole, the ion conductivity becomes insufficient. Above 30% by mole, the film strength drops. Excellent oxygen pump performance can be obtained by adding precious metal to the electrode under layer made of a zirconia solid electrolyte to which one or more of yttria, magnesia, ceria, and scandia are added. It is preferable that this precious metal is any one of Pt, Pd, Ir, Au, Ru, and Rh, or an alloy thereof.

The precious metal to be added can be selected according to the gas to be treated by the oxygen pumping cell. For example, when NOx are converted (reduced or oxidized) into NO or $NO_2$ on the first electrode, the electrode under layer under the first electrode desirably contains precious metal elements active to NOx, such as Rh, Au, Pt—Rh alloys, and Ir—Rh alloys.

On the other hand, when HC and CO are oxidized and eliminated on the first electrode, ones active to these reducing gases, such as Pt, Pd, Ir, Ru, and alloys thereof, are desirably used. In this way, the addition of precious metal to the electrode base layer increases the activity of the electrode interface, further enhancing the adhesion to the substrate and allowing a significant improvement in oxygen pumping performance. Powdered precious metals to be added to the electrode under layer favorably have a particle size of 5 $\mu$m or less, and preferably 3 $\mu$m or less. At or above 5 $\mu$m, the three-phase interface occupied by the powdered precious metals added may decrease significantly, failing to improve the electrode activity.

The content of these powered precious metals desirably falls within the range of 0.05–5% by weight, and preferably 0.1–2% by weight, with respect to the total amount of the electrode under layer. When the content falls below 0.05% by weight, the precious metals provide no significant effect. Above 5% by weight, in contrast, the precious metals agglomerate to decrease the effect of the addition.

Moreover, this electrode under layer desirably has a voidage of 5–40% by volume and an average thickness of 3–30 $\mu$m.

This electrode under layer can be formed by application using an appropriate method such as ordinary screen printing. In the printing-based formation, the above-described powdered precious metals and a powdered solid electrolyte are mixed with an organic binder, an organic solvent, a dispersant, and the like, into a paste for use. Here, such factors as the amount of the solvent and the diameters of the power particles can be controlled to adjust the porosity of the electrode under layer 9. The thickness of the electrode under layer 9 can also be adjusted by changing the viscosity of this slurry, the printing condition, and so on.

The oxygen pumping cell of the present invention is effectively used as a NOx converting pump cell or a reducing-gas oxidizing pump cell in particular. Then, the configuration of a NOx sensor for total NOx concentration measurement comprising the gas sensing device and the oxygen pumping cell of the present invention will hereinafter be described in detail with reference to the drawings. In the drawings, the same reference numerals designate identical parts.

Figure 4:
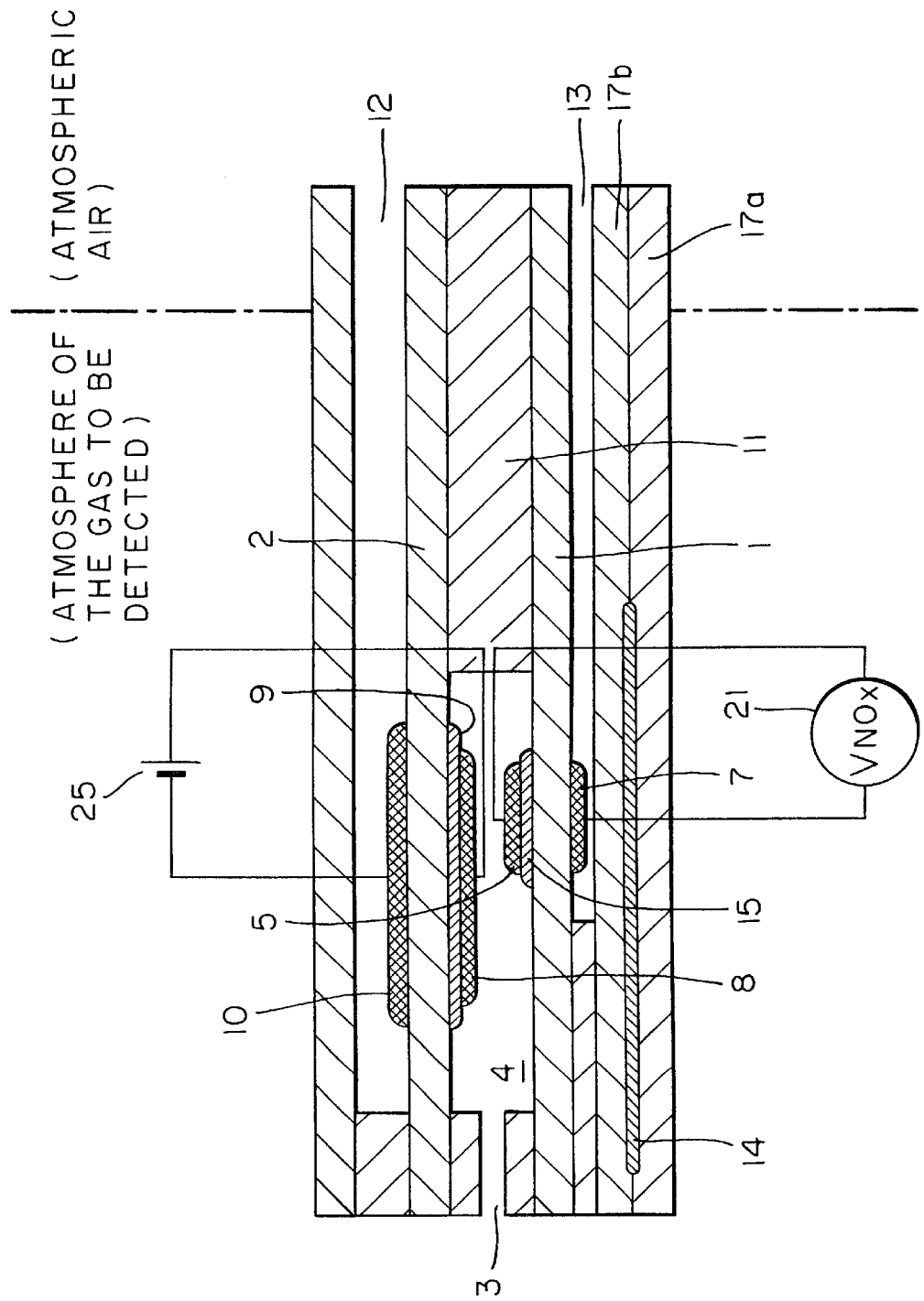
FIG. 4 shows a cross sectional view of an embodiment of the sensor structure having the sensing device and oxygen pumping cell according to the present invention.

A total NOx sensor shown in FIG. 4 is a NOx gas sensor comprising a gas measurement chamber 4, a gas inlet 3, a NOx detection device, a NOx conversion pump cell, means 21, and voltage applying means 25. The gas measurement chamber 4 has an internal space that is formed by fixing a first solid electrolyte substrate 1 having oxygen ion conductivity and an opposed second solid electrolyte substrate 2 also having oxygen ion conductivity by a spacer 11 with a predetermined distance between the solid electrolyte substrates 1 and 2. The gas inlet 3 is formed so that the atmosphere of a gas to be detected flows into the gas measurement chamber 4 with a predetermined gas diffusion resistance. The NOx sensing device is composed of: an electrode under layer 15 fixed onto the first solid electrolyte substrate 1 to be exposed to an atmosphere inside the gas measurement chamber 4; a sensing electrode 5 active to NOx and oxygen, fixed onto the electrode under layer 15; and a reference electrode 7 active to at least oxygen. The NOx conversion pump cell is composed of: an electrode under layer 9 fixed onto the second solid electrolyte substrate 2 to be exposed to the atmosphere inside the gas measurement chamber 4; a NOx conversion electrode 8 for converting NO in the gas to be detected into $NO_{21}$ or $NO_2$ into NO; and a NOx conversion counter electrode 10 active to oxygen, fixed onto the second solid electrolyte substrate 2 so as to be exposed to an atmosphere containing oxygen or oxygenated compound gas. The NOx conversion electrode 8 is active to NOx and oxygen, and fixed onto the electrode under layer 9. The means 21 measures a potential difference $V_{NOx}$ between the sensing electrode 5 and the reference electrode 7. The voltage applying means 25 drives the NOx conversion pump cell. Here, a predetermined voltage is applied to the NOx conversion pump cell while the potential difference $V_{NOx}$ between the sensing electrode 5 and the reference electrode 7 is detected so that this potential difference is used as a signal representing the concentration of NOx in the gas to be detected. In FIG. 4, the electrode under layers 15 and 9 are arranged both between the first solid electrolyte substrate 1 and the sensing electrode 5 and between the second solid electrolyte substrate 2 and the NOx conversion electrode 8. However, either one of the electrode base layers may be arranged exclusively. Otherwise, the electrode under layers may be arranged between the first solid electrolyte substrate 1 and the reference electrode 7 and/or between the second solid electrolyte substrate 2 and the NOx conversion counter electrode 10.

FIG. 4 shows an example of structure in which means for heating the sensor device, or heater substrates 17a and 17b sandwiching a heater 14, are laminated and bonded to the sensor device. To control the device heating temperature, a thick film of thermocouple is printed in the vicinity of the sensing electrode 5, the reference electrode 7, the NOx conversion electrode 8, and so on. A temperature signal of this thermocouple is used to drive the heater for feedback control. Otherwise, an alternating voltage may be imposed on the NOx conversion pump cell (8, 10) to measure the second solid electrolyte substrate 2 of the NOx conversion pump cell for a bulk impedance, which can be used as a heater controlling signal. Note that in the present invention, the heating means are not particularly restricted. The sensor device may be put in an electric furnace or a heater tube that is installed separately.

Incidentally, the first and second solid electrolyte substrates 1 and 2 are favorably made of a zirconia solid electrolyte as described above. The spacer 11 is also favorably made of the same zirconia solid electrolyte. Moreover, in the case of fabricating the sensor device that incorporates the self-heating heater, the heater substrates 17a and 17b may also be made of a zirconia solid electrolyte. In this case, alumina layers or the like high in electrical insulation should be formed between the heater 14 and the heater substrates 17a, 17b to prevent the zirconia solid electrolytes from electrochemical reduction and degradation.

In the configuration of the NOx sensor shown in FIG. 4, the electrochemical oxygen pumping cell (conversion pump cell 8, 10) is used to convert NOx in the gas to be detected, i.e., NO and $NO_2$ in combustion exhaust into a single gas NO or $NO_2$ for total NOx detection. Such single-gas conversion using the conversion pump cell is effected by introducing oxygen into the gas measurement chamber 4 from exterior or ejecting oxygen from the gas measurement chamber 4. On that occasion, NO is oxidized or $NO_2$ is reduced by the conversion electrode 8 which is active to NOx. In the configuration of FIG. 4, the conversion counter electrode 10 is placed in an air introducing duct 12 to pump oxygen from the air. Alternatively, the conversion counter electrode 10 may be exposed to the atmosphere of the gas to be detected, so that oxygen or oxygenated compounds in the gas to be detected are electrochemically decomposed for oxygen pumping. Typically, $CO_2$, CO, $H_2O$, and the like apply to the oxygenated compounds in the gas to be detected.

Here, the configuration of the sensing electrode part and the conversion electrode part to have the electrode under layers of the present invention allows significant remedies against the abnormality, drift, and the like of the sensor output resulting from electrode cracks, exfoliation, and so on. Besides, it is possible to control the electrochemical activity of the interfaces between the electrodes and the solid electrolytes. The sensor of such a laminated structure has internal spaces including the gas measurement chamber 4. Thus, while conventional electrode configurations are vulnerable to a short between electrodes due to electrode exfoliation, the electrode configuration of the present invention provides significant improvements.

In FIG. 4, a single gas inlet 3 is formed in a surface of the gas measurement chamber. Needless to say, a plurality of inlets may be formed in other substrate surfaces. The gas inlet may be made of a porous member.
Moreover, the gas path of the gas inlet may be filled with a porous catalyst for the sake of higher gas treatment effects. Incidentally, in the total NOx sensor structure of the present invention, it is preferable in terms of gas response that the gas inlet is free from ventilation resistance such as determines the rate of gas diffusion.

Figure 5:
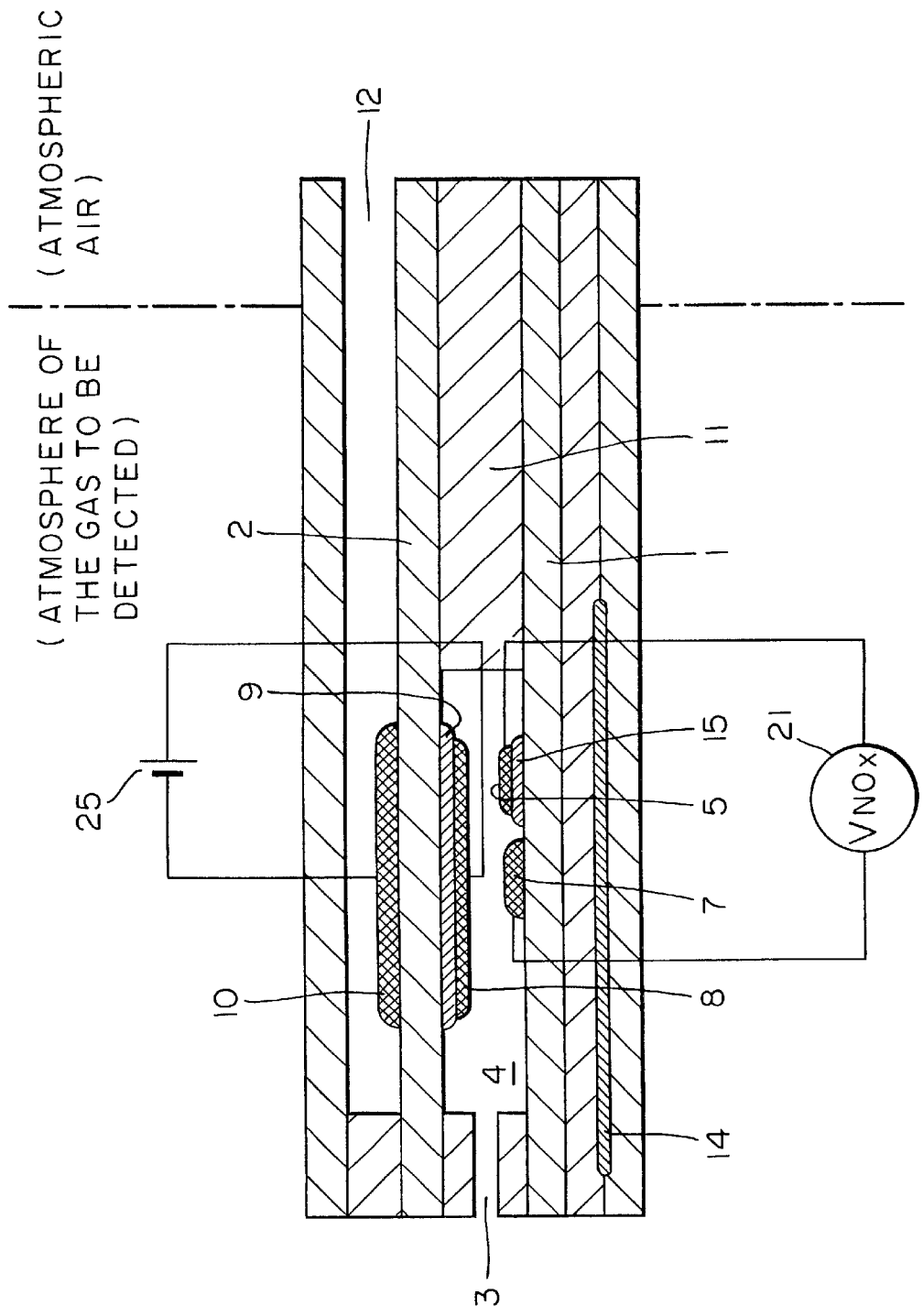
FIG. 5 shows a cross sectional view of another embodiment of the sensor structure having the sensing device and oxygen pumping cell according to the present invention.

FIG. 5 shows a NOx sensor having a structure in which the reference electrode 7 is arranged in the gas measurement chamber 4. Here, the reference electrode 7 must be active to oxygen and inactive at least to NOx. As employed herein, being inactive refers to having an electrode potential smaller than that of the sensing electrode at least with respect to an identical NOx concentration. It is obvious that such a system capable of arranging the reference electrode 7 in the same atmosphere of the gas to be detected is characteristic of a mixed potential type sensor in particular. This reference electrode 7 is desirably arranged in the vicinity of the sensing electrode 5.

Figure 6:
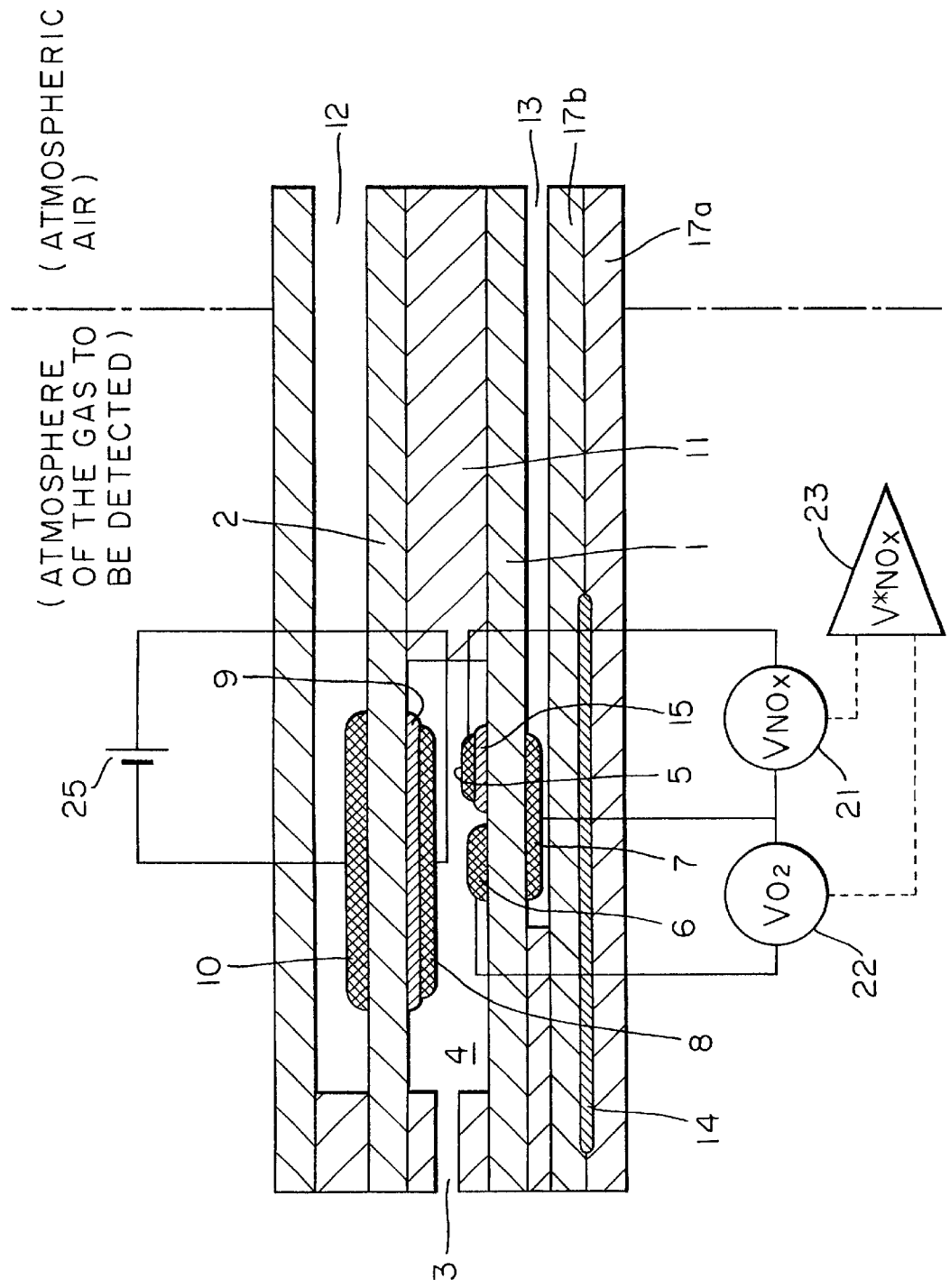
FIG. 6 shows a cross sectional view of another embodiment of the sensor structure having the sensing device and oxygen pumping cell according to the present invention.

FIG. 6 shows a NOx sensor having a configuration in which an oxygen sensing electrode 6 which is active to oxygen and inactive to at least NOx is arranged in the gas measurement chamber 4, and the reference electrode 7 to be shared with the sensing electrode 5 is arranged in an air reference duct 13. Needless to say, this reference electrode 7 may be separately provided for each of the sensing electrodes. In this configuration, arithmetic processing means 23 corrects variations in oxygen concentration by using both a potential difference $V_{O2}$ between the reference electrode 7 and the oxygen sensing electrode 6 and a potential difference $V_{NOx}$ between the reference electrode 7 and the sensing electrode 5. The arithmetic processing means 23 is realized by hardware using an electronic circuit, or software using a microcomputer or the like. This allows accurate NOx detection even when variations in the oxygen concentration of the atmosphere of the gas to be detected affect variations in the oxygen concentration inside the gas measurement chamber.

Figure 7:
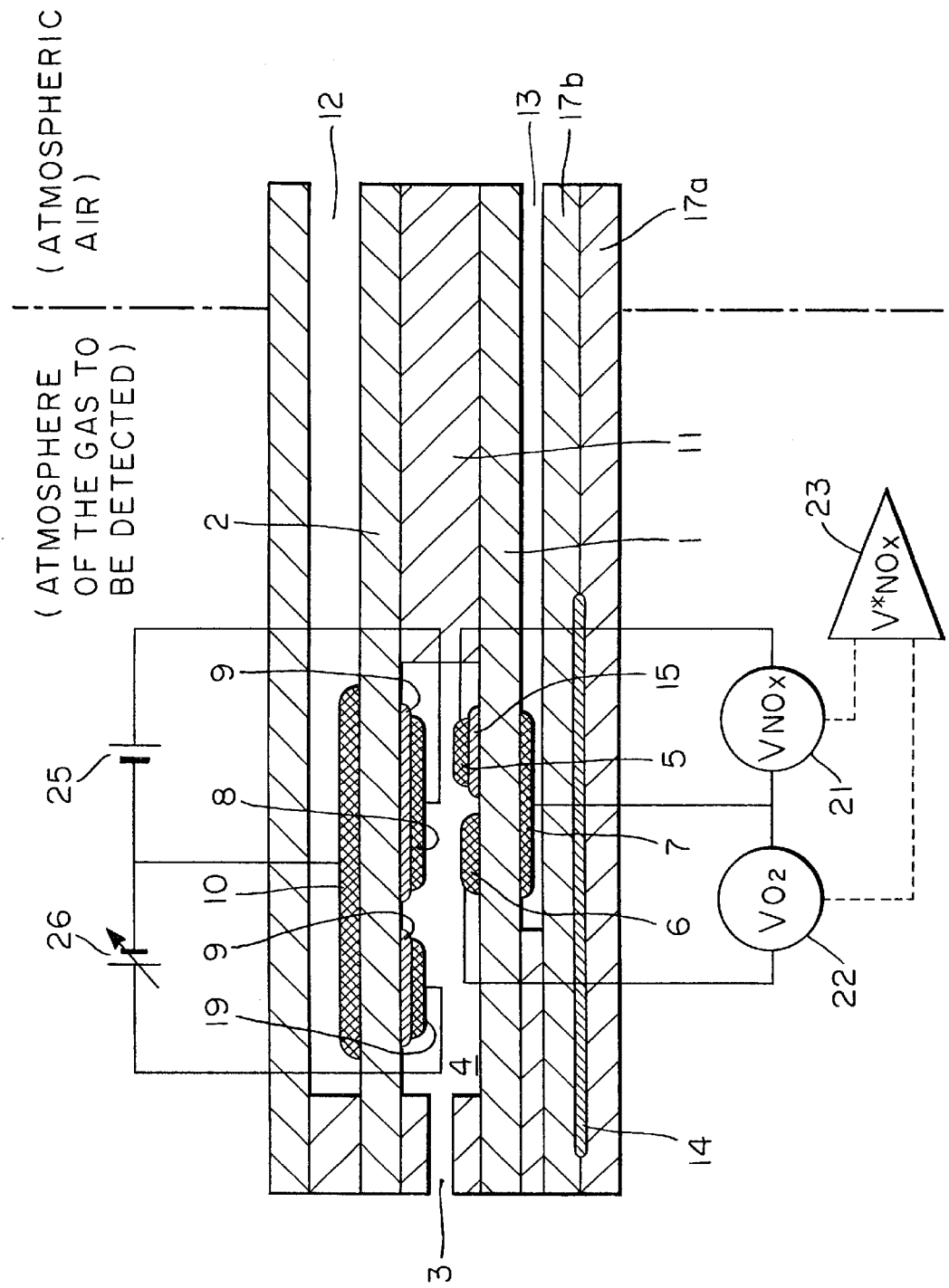
FIG. 7 shows a cross sectional view of another embodiment of the sensor structure having the sensing device and oxygen pumping cell according to the present invention.

FIG. 7 shows the NOx sensor having the configuration of FIG. 6, further comprising a gas treatment electrode 19 for applying oxidization to reducing gases in the atmosphere of the gas to be detected, such as CO and HC in combustion exhaust, at the prior stage of the gas measurement chamber 4. Here, the electrode under layer 9 is also formed under the gas treatment electrode 19. In FIG. 7, the counter electrode 10 is shared with the NOx conversion electrode 8, whereas counter electrodes may be arranged separately.

This gas treatment electrode 19 is desirably active to HC and CO mentioned above. An external power supply 26 is provided as means for applying a voltage to the gas treatment pump cell that is composed of the gas treatment electrode 19 and the counter electrode 10 thereof. Incidentally, although not shown in FIG. 7, a gas resistor or a gas vent may be arranged between the gas treatment electrode 19 and the NOx conversion electrode 8 so that the gas measurement chamber 4 has a front chamber and a rear chamber, or a double-chamber structure. This double-chamber structure further suppresses variations in the oxygen concentration of a gas conversion chamber (rear chamber), thereby improving the sensor characteristics.

Figure 8:
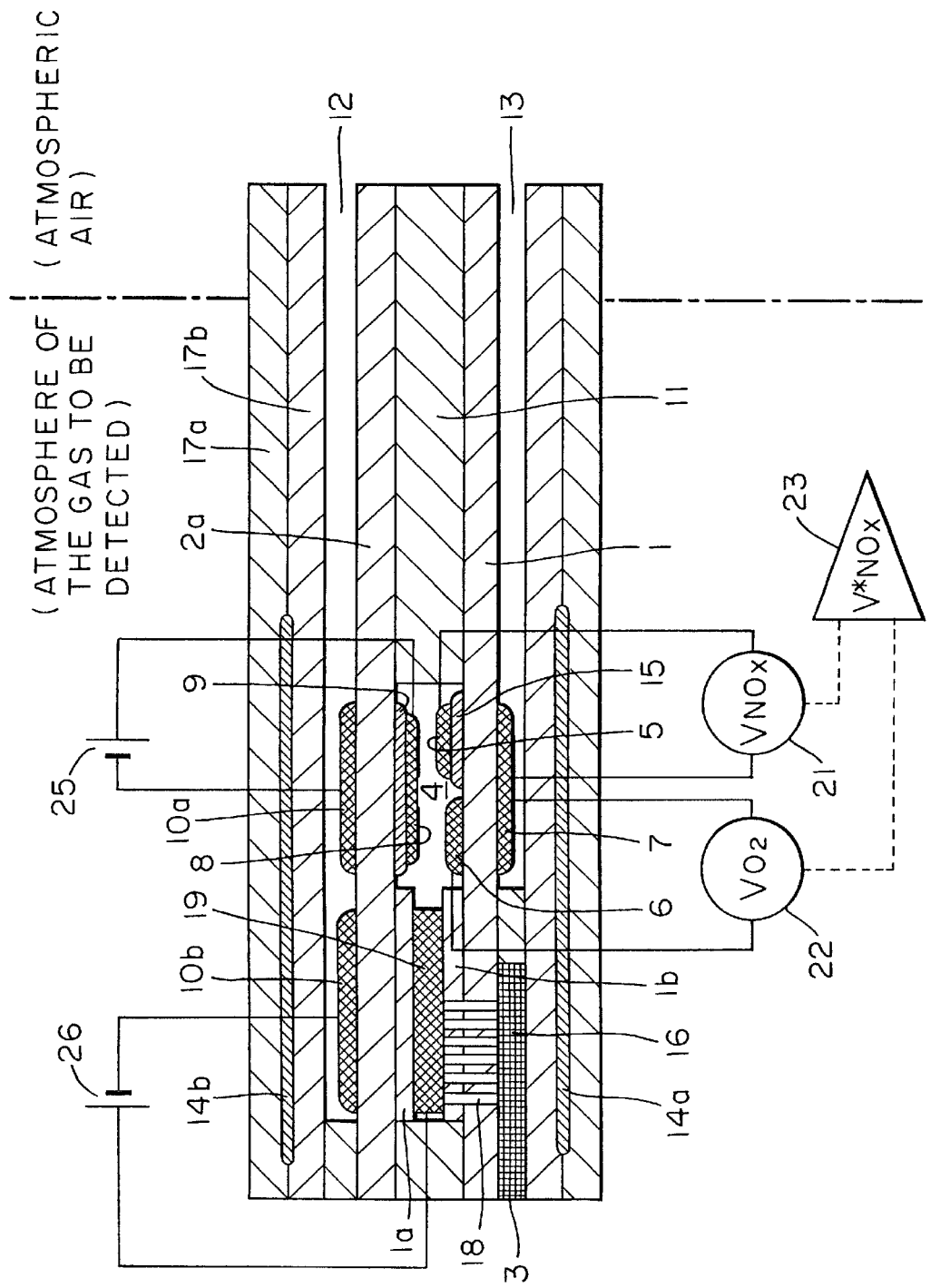
FIG. 8 shows a cross sectional view of another embodiment of the sensor structure having the sensing device and oxygen pumping cell according to the present invention.

FIG. 8 shows a NOx sensor having a configuration in which a plurality of gas diffusion holes 18 are formed in the solid electrolyte substrate 1 where the sensing electrode is arranged. The preceding gas path is filled with a catalytic porous member 16. The gas to be detected is introduced through the gas inlet 3. The gas treatment electrode 19 is made of a porous film and held between solid electrolyte substrates 1b and 2b. Porosities are set so as to prevent the gas ventilation resistances from determining the rate of gas diffusion even in such a structure. In FIG. 8, a counter electrode 10b of the gas treatment electrode 19 is arranged independent of a conversion counter electrode 10a of the NOx conversion electrode 8. To heat the sensor device more evenly, heaters (14a, 14b) are provided at the top and bottom, two positions.

REFERENTIAL EXAMPLES

Hereinafter, description will be given of embodiments to which the electrode under layers of the present invention are applied, or ones of the sensing device, oxygen pumping cell, and sensor for NOx measurement in particular. In advance of the embodiments, various materials were examined for NOx activity.

Green sheets of yttria-added (6% by mole) zirconia solid electrolyte (250 $\mu$m in thickness) fabricated by the above-described method were cut into rectangles. Pt lead conductors were formed thereon by screen printing. Then, various materials shown in Table 1 were screen-printed to form sensing electrodes. Reference electrodes made of Pt were similarly screen-printed on the other sides of the green sheets. These sensor devices were degreased in the air at approximately 500° C. before sintered at approximately 1400° C. After sintered, each sensor device was bonded with lead wires to fabricate a sample, which was set into a quartz tube held in an electric furnace and evaluated for activity to NOx under an oxygen concentration of 5%. Here, NO gas of 100 ppm and $NO_2$ gas of 100 ppm were used as NOx. The atmosphere in the electric furnace was controlled to a temperature of 600° C. The outputs of each sample with respect to NOx were evaluated by using a voltmeter having a high input impedance. Here, the sensing and reference electrodes were placed in the same atmosphere. Pt was independently examined for activity to NOx, in terms of the outputs (mixed potentials) of a sensing electrode by using a closed-ended zirconia solid electrolyte tube. The result proved that Pt has no sensitivity to either of NO and $NO_2$. Here, the atmosphere inside the zirconia tube was the air, and the atmosphere outside the same was the gas to be detected.

Table 1 collectively shows the results. It is confirmed that the precious metal materials of group A shown in Table 1 exhibit no sensitivity to NOx, and have no NOx activity as an electrode. In contrast, the precious metal materials of group B exhibit high activity to NOx. The metal oxide materials of group C show excellent NOx sensitivities. Among them, those oxide materials containing Cr are found to exhibit high sensitivity characteristics. It is also found that $NiCr_2O_4$, $FeCr_2O_4$, $MgCr_2O_4$, and $Cr_2O_3$ have particularly high sensitivity characteristics. Accordingly, it is shown that the precious metal materials of group B are used as the first precious metal of the present invention, and the precious metal materials of group A are used as the second precious metal.

Pt—Rh (3% by weight) shown in group B' was an alloy of Pt, a precious metal of group A, and Rh, a precious metal of group B. This alloy was found to have high sensitivity characteristics to NOx.

TABLE 1

| | Material for sensing electrode | $NO_2$(100 ppm) | NO(100 ppm) |
|---|---|---|---|
| A | Pt | 0 mV | 0 mV |
| | Pd | 0 mV | 0 mV |
| | Pt—Pd(10 wt %) | 0 mV | 0 mV |
| | Pd—Ru(5 wt %) | 0 mV | 0 mV |
| B | Ir | 42 mV | −12 mV |
| | Au | 51 mV | −13 mV |
| | Rh | 60 mV | −15 mV |
| | Ir—Au(10 wt %) | 60 mV | −15 mV |
| | Ir—Rh(5 wt %) | 73 mV | −16 mV |
| | Au—Rh(5 wt %) | 68 mV | −14 mV |
| B' | Pt—Rh(3 wt %) | 95 mV | −23 mV |
| C | NiO | 78 mV | −18 mV |
| | $WO_3$ | 56 mV | −11 mV |
| | $Cr_2O_3$ | 96 mV | −25 mV |
| | $NiCr_2O_4$ | 103 mV | −31 mV |
| | $FeCr_2O_4$ | 97 mV | −27 mV |
| | $MgCr_2O_4$ | 95 mV | −25 mV |
| | $CrMnO_3$ | 70 mV | −13 mV |
| | $CrWO_4$ | 68 mV | −12 mV |
| | $LaCrO_3$ | 58 mV | −12 mV |
| | $NiTiO_3$ | 47 mV | −11 mV |
| | $FeTiO_3$ | 51 mV | −13 mV |
| | $ZnFe_2O_4$ | 61 mV | −14 mV |

Example 1

Figure 2:
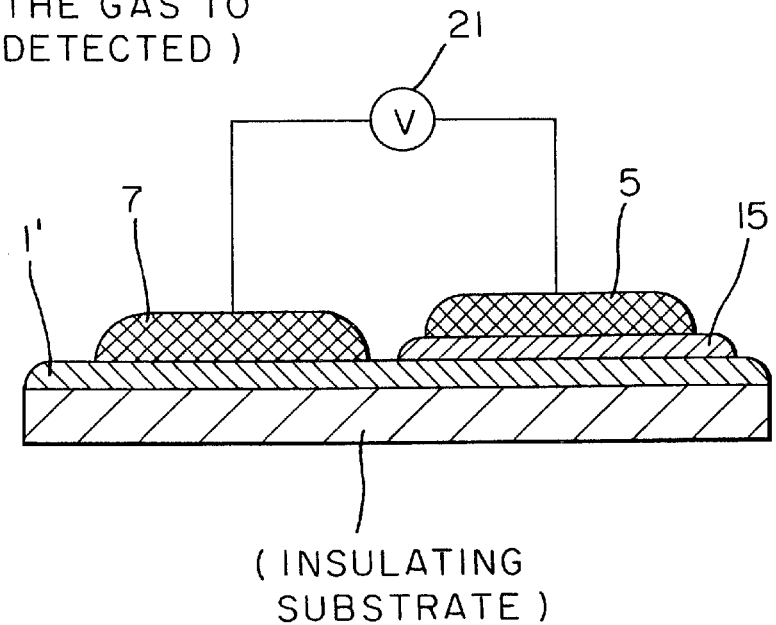
FIG. 2 shows a cross sectional view of another embodiment of the sensing device structure according to the present invention.

NOx sensing devices having the structure of FIG. 1, in which an electrode under layer is arranged between a solid electrolyte substrate 1 and a sensing electrode 5, were fabricated by the same method as the referential examples were. Here, the solid electrolyte substrates 1 and the electrode under layers 15 were made of the materials shown in Table 2. No Precious metal was added to the electrode under layer. Three types of sensing electrodes 5, or Pt—Rh (3% by weight), $Cr_2O_3$, and $NiCr_2O_4$, were prepared. The reference electrodes 7 were made of Pt. Like the referential examples, the obtained samples were put in an electric furnace and evaluated for sensitivity characteristics to $NO_2$ (100 ppm). The sensitivity characteristics examined were initial sensitivity and the rate of change of sensitivity (the rate of change of drift) under a predetermined accelerate condition. Besides, immediately after the fabrication, each sample was examined for the conditions of the electrode films by eye observation and under an optical stereomicroscope. For the sake of comparison, samples having no electrode under layer were also prepared.

Table 2 collectively shows the results. Here, the initial sensitivity is a difference between the base output in the presence of 5-vol % oxygen ($N_2$ the rest) and the sensor output in the presence of 5-vol % oxygen ($N_2$ the rest) with $NO_2$ (100 ppm). The rate of change of drift shows the ratio of a difference (the amount of change) between the sensitivity to $NO_2$ (100 ppm) after a predetermined acceleration test and the initial sensitivity, to the initial sensitivity. The symbol + indicates an increase in sensitivity, and the symbol − a decrease in sensitivity.

The results reveal that as compared to the conventional samples (comparative examples) having no electrode under layer, the samples of this example having an electrode under layer made of a zirconia solid electrolyte that contains yttria of or below 3% by mole, or non-yttria stabilizers, show little drop in sensitivity and can be reduced to ½ or so in the rate of change of drift. Incidentally, a yttria stabilizer of 3% or less by mole may lower the sensitivity characteristics in the absence of other stabilizers. Yttria of 5% or more by mole increases the change of drift even if other stabilizers are added. Stereomicroscopic observations on the electrode films of the respective samples found minute cracks and/or film exfoliation in the samples having 12-mol %-MgO-added zirconia substrates. This shows that the zirconia solid electrolyte substrate is preferably made of a yttria-added zirconia solid electrolyte.

TABLE 2

| | Sensing electrode part | | $NO_2$(100 ppm) | |
|---|---|---|---|---|
| Material for solid electrolyte Substrate | Stabilizer added to zirconia electrode under layer | Material for sensing electrode | Initial sensitivity | Rate of change of drift |
| 6 mol % $Y_2O_3$—$ZrO_2$ | No under layer | Pt—Rh(3 wt %) | 84 mV | +98% |
| 6 mol % $Y_2O_3$—$ZrO_2$ | No under layer | $Cr_2O_3$ | 91 mV | +85% |
| 6 mol % $Y_2O_3$—$ZrO_2$ | No under layer | $NiCr_2O_4$ | 93 mV | +91% |
| 6 mol % $Y_2O_3$—$ZrO_2$ | 5 mol % $Y_2O_3$ | Pt—Rh(3 wt %) | 96 mV | +95% |
| 6 mol % $Y_2O_3$—$ZrO_2$ | 5 mol % $Y_2O_3$ | $Cr_2O_3$ | 103 mV | +92% |
| 6 mol % $Y_2O_3$—$ZrO_2$ | 5 mol % $Y_2O_3$ | $NiCr_2O_4$ | 98 mV | +88% |
| 6 mol % $Y_2O_3$—$ZrO_2$ | 3 mol % $Y_2O_3$ | Pt—Rh(3 wt %) | 73 mV | +66% |
| 6 mol % $Y_2O_3$—$ZrO_2$ | 3 mol % $Y_2O_3$ | $Cr_2O_3$ | 67 mV | +57% |
| 6 mol % $Y_2O_3$—$ZrO_2$ | 3 mol % $Y_2O_3$ | $NiCr_2O_4$ | 64 mV | +53% |
| 6 mol % $Y_2O_3$—$ZrO_2$ | 2 mol % $Y_2O_3$ | Pt—Rh(3 wt %) | 34 mV | +46% |
| 6 mol % $Y_2O_3$—$ZrO_2$ | 2 mol % $Y_2O_3$ | $Cr_2O_3$ | 41 mV | +45% |
| 6 mol % $Y_2O_3$—$ZrO_2$ | 2 mol % $Y_2O_3$ | $NiCr_2O_4$ | 29 mV | +48% |
| 6 mol % $Y_2O_3$—$ZrO_2$ | 1 mol % $Y_2O_3$ | Pt—Rh(3 wt %) | 21 mV | +39% |

TABLE 2-continued

| Material for solid electrolyte Substrate | Stabilizer added to zirconia electrode under layer | Material for sensing electrode | Initial sensitivity | Rate of change of drift |
|---|---|---|---|---|
| 6 mol % $Y_2O_3$—$ZrO_2$ | 1 mol % $Y_2O_3$ | $Cr_2O_3$ | 29 mV | +54% |
| 6 mol % $Y_2O_3$—$ZrO_2$ | 1 mol % $Y_2O_3$ | $NiCr_2O_4$ | 18 mV | +46% |
| 6 mol % $Y_2O_3$—$ZrO_2$ | 5 mol % $Y_2O_3$ + 8 mol % $CeO_2$ | Pt—Rh(3 wt %) | 89 mV | +88% |
| 6 mol % $Y_2O_3$—$ZrO_2$ | 5 mol % $Y_2O_3$ + 8 mol % $CeO_2$ | $Cr_2O_3$ | 96 mV | +85% |
| 6 mol % $Y_2O_3$—$ZrO_2$ | 5 mol % $Y_2O_3$ + 8 mol % $CeO_2$ | $NiCr_2O_4$ | 98 mV | +90% |
| 6 mol % $Y_2O_3$—$ZrO_2$ | 3 mol % $Y_2O_3$ + 8 mol % $CeO_2$ | Pt—Rh(3 wt %) | 92 mV | +48% |
| 6 mol % $Y_2O_3$—$ZrO_2$ | 3 mol % $Y_2O_3$ + 8 mol % $CeO_2$ | $Cr_2O_3$ | 97 mV | +42% |
| 6 mol % $Y_2O_3$—$ZrO_2$ | 3 mol % $Y_2O_3$ + 8 mol % $CeO_2$ | $NiCr_2O_4$ | 96 mV | +45% |
| 6 mol % $Y_2O_3$—$ZrO_2$ | 2 mol % $Y_2O_3$ + 8 mol % $CeO_2$ | Pt—Rh(3 wt %) | 92 mV | +45% |
| 6 mol % $Y_2O_3$—$ZrO_2$ | 2 mol % $Y_2O_3$ + 8 mol % $CeO_2$ | $Cr_2O_3$ | 101 mV | +37% |
| 6 mol % $Y_2O_3$—$ZrO_2$ | 2 mol % $Y_2O_3$ + 8 mol % $CeO_2$ | $NiCr_2O_4$ | 99 mV | +39% |
| 6 mol % $Y_2O_3$—$ZrO_2$ | 1 mol % $Y_2O_3$ + 8 mol % $CeO_2$ | Pt—Rh(3 wt %) | 96 mV | +42% |
| 6 mol % $Y_2O_3$—$ZrO_2$ | 1 mol % $Y_2O_3$ + 8 mol % $CeO_2$ | $Cr_2O_3$ | 102 mV | +40% |
| 6 mol % $Y_2O_3$—$ZrO_2$ | 1 mol % $Y_2O_3$ + 8 mol % $CeO_2$ | $NiCr_2O_4$ | 96 mV | +42% |
| 6 mol % $Y_2O_3$—$ZrO_2$ | 8 mol % $CeO_2$ | Pt—Rh(3 wt %) | 91 mV | +43% |
| 6 mol % $Y_2O_3$—$ZrO_2$ | 8 mol % $CeO_2$ | $Cr_2O_3$ | 98 mV | +39% |
| 6 mol % $Y_2O_3$—$ZrO_2$ | 8 mol % $CeO_2$ | $NiCr_2O_4$ | 97 mV | +43% |
| 12 mol % MgO—$ZrO_2$ | 5 mol % $Y_2O_3$ + 8 mol % $CeO_2$ | Pt—Rh(3 wt %) | 87 mV | +82% |
| 12 mol % MgO—$ZrO_2$ | 5 mol % $Y_2O_3$ + 8 mol % $CeO_2$ | $Cr_2O_3$ | 93 mV | +88% |
| 12 mol % MgO—$ZrO_2$ | 5 mol % $Y_2O_3$ + 8 mol % $CeO_2$ | $NiCr_2O_4$ | 96 mV | +93% |
| 12 mol % MgO—$ZrO_2$ | 3 mol % $Y_2O_3$ + 8 mol % $CeO_2$ | Pt—Rh(3 wt %) | 92 mV | +46% |
| 12 mol % MgO—$ZrO_2$ | 3 mol % $Y_2O_3$ + 8 mol % $CeO_2$ | $Cr_2O_3$ | 95 mV | +37% |
| 12 mol % MgO—$ZrO_2$ | 3 mol % $Y_2O_3$ + 8 mol % $CeO_2$ | $NiCr_2O_4$ | 97 mV | +43% |
| 12 mol % MgO—$ZrO_2$ | 2 mol % $Y_2O_3$ + 8 mol % $CeO_2$ | Pt—Rh(3 wt %) | 96 mV | +38% |
| 12 mol % MgO—$ZrO_2$ | 2 mol % $Y_2O_3$ + 8 mol % $CeO_2$ | $Cr_2O_3$ | 98 mV | +35% |
| 12 mol % MgO—$ZrO_2$ | 2 mol % $Y_2O_3$ + 8 mol % $CeO_2$ | $NiCr_2O_4$ | 96 mV | +34% |
| 12 mol % MgO—$ZrO_2$ | 1 mol % $Y_2O_3$ + 8 mol % $CeO_2$ | Pt—Rh(3 wt %) | 96 mV | +43% |
| 12 mol % MgO—$ZrO_2$ | 1 mol % $Y_2O_3$ + 8 mol % $CeO_2$ | $Cr_2O_3$ | 100 mV | +43% |
| 12 mol % MgO—$ZrO_2$ | 1 mol % $Y_2O_3$ + 8 mol % $CeO_2$ | $NiCr_2O_4$ | 98 mV | +41% |
| 12 mol % MgO—$ZrO_2$ | 8 mol % $CeO_2$ | Pt—Rh(3 wt %) | 97 mV | +44% |
| 12 mol % MgO—$ZrO_2$ | 8 mol % $CeO_2$ | $Cr_2O_3$ | 98 mV | +40% |
| 12 mol % MgO—$ZrO_2$ | 8 mol % $CeO_2$ | $NiCr_2O_4$ | 100 mV | +43% |

Example 2

NOx sensing devices having the structure of FIG. 1 were fabricated as in the example 1. Here, the electrode under layers and sensing electrodes were made of the materials shown in Table 3. The solid electrolyte substrates were zirconia solid electrolyte substrates containing 6-mol % yttria. The reference electrodes 7 were made of Pt. The obtained samples were evaluated for sensitivity characteristics and film conditions as in the example 1. To check the effects of the electrode under layers, samples having no electrode under layer were also prepared.

Table 3 shows the results. It is found that as compared to the conventional samples (comparative examples) having no electrode under layer, the electrodes of this example show little drop in initial sensitivity and can be reduced to or below ½ in the rate of change of drift. In particular, zirconia solid electrolytes that contain ceria, magnesia, or scandia as a stabilizer can be used as the electrode under layers with a further reduction in drift. The drift suppressing effect was also observed in the electrode under layers combining a plurality of stabilizers. Stereomicroscopic observations on the electrode films confirmed that while partial exfoliations were found in the comparative examples having no electrode under layer, favorable films were obtained from the example samples of the present invention.

TABLE 3

| Stabilizer added to zirconia electrode under layer | Material for sensing electrode | Initial sensitivity | Rate of change of drift |
|---|---|---|---|
| No under layer | Pt—Rh(3 wt %) | 86 mV | +95% |
| No under layer | $Cr_2O_3$ | 93 mV | +88% |
| No under layer | $NiCr_2O_4$ | 89 mV | +86% |
| No under layer | $FeCr_2O_4$ | 97 mV | +102% |
| No under layer | $MgCr_2O_4$ | 95 mV | +83% |
| 15 mol % MgO | Pt—Rh(3 wt %) | 91 mV | +37% |
| 15 mol % MgO | $Cr_2O_3$ | 98 mV | +38% |
| 15 mol % MgO | $NiCr_2O_4$ | 102 mV | +42% |
| 15 mol % MgO | $FeCr_2O_4$ | 92 mV | +36% |
| 15 mol % MgO | $MgCr_2O_4$ | 88 mV | +42% |
| 12 mol % $CeO_2$ | Pt—Rh(3 wt %) | 97 mV | +32% |
| 12 mol % $CeO_2$ | $Cr_2O_3$ | 95 mV | +34% |
| 12 mol % $CeO_2$ | $NiCr_2O_4$ | 101 mV | +35% |
| 12 mol % $CeO_2$ | $FeCr_2O_4$ | 90 mV | +38% |
| 12 mol % $CeO_2$ | $MgCr_2O_4$ | 89 mV | +45% |
| 15 mol % $Sc_2O_3$ | Pt—Rh(3 wt %) | 87 mV | +41% |
| 15 mol % $Sc_2O_3$ | $Cr_2O_3$ | 93 mV | +35% |
| 15 mol % $Sc_2O_3$ | $NiCr_2O_4$ | 94 mV | +39% |
| 15 mol % $Sc_2O_3$ | $FeCr_2O_4$ | 91 mV | +38% |
| 15 mol % $Sc_2O_3$ | $MgCr_2O_4$ | 84 mV | +35% |
| 12 mol % $Sc_2O_3$-2 mol % CaO | $Cr_2O_3$ | 85 mV | +41% |
| 12 mol % $Sc_2O_3$-2 mol % $CeO_2$ | $Cr_2O_3$ | 91 mV | +39% |
| 12 mol % $CeO_2$-2 mol % CaO | $Cr_2O_3$ | 93 mV | +42% |
| 12 mol % $CeO_2$-2 mol % MgO | $Cr_2O_3$ | 96 mV | +36% |
| 12 mol % CaO | $Cr_2O_3$ | 80 mV | +54% |
| 10 mol % $ThO_2$ | $Cr_2O_3$ | 75 mV | +57% |
| 10 mol % $Yb_2O_3$ | $Cr_2O_3$ | 70 mV | +61% |

Example 3

NOx sensing devices having the structure of FIG. 1 were fabricated as in the example 1. Here, the solid electrolyte substrates, the electrode under layers and sensing electrodes were made of the materials shown in Table 4. The solid electrolyte substrates were zirconia solid electrolyte substrates containing 6-mol % yttria or 12-mol % magnesia. Moreover, the electrode under layer were zirconia solid electrolyte containing 8-mol % yttria as stabilizer and 0.7 wt % Pt as precious metal. Three types of sensing electrodes 5, or Pt—Rh (3% by weight), $Cr_2O_3$, and $NiCr_2O_4$, were prepared. The reference electrodes 7 were made of Pt. The obtained samples were evaluated for sensitivity characteristics and film conditions as in the example 1. To check the effects of the electrode under layers, samples having no electrode under layer were also prepared. Moreover, to check the effects of the addition of precious metal, samples having electrode under layer without Pt were also prepared.

Table 4 shows the results. The change rates of drift of the samples having electrode under layer made of zirconia solid electrolyte which contains only 8-mol % yttria were as high as those of the conventional samples (comparative examples) having no electrode under layer. This shows that the drift suppressing effect was not realized in the electrode under layer containing only yttria. Addition of Pt to the electrode under layer made of zirconia solid electrolyte that contains only yttria shows little drop in initial sensitivity and allows a significant reduction in the rate of change of drift. The drift suppressing effect was also observed in the samples having 12-mol %-MgO-added zirconia substrates.

Stereomicroscopic observations on the electrode films of the respective samples found minute cracks and/or film exfoliation in the samples having 12-mol %-MgO-added zirconia substrates. This shows that the zirconia solid electrolyte substrate is preferably made of a yttria-added zirconia solid electrolyte.

Table 5 shows the results. It is found that as compared to the conventional samples (comparative examples) having no electrode under layer, the electrodes of this example show little drop in initial sensitivity and can be reduced to or below ½ in the rate of change of drift. In particular, zirconia solid electrolytes that contain magnesia, ceria, yttria, or scandia as a stabilizer can be used as the electrode under layers with a further reduction in drift. The drift suppressing effect was also observed in the electrode under layers combining a plurality of stabilizers. Stereomicroscopic observations on the electrode films confirmed that while partial exfoliations were found in the comparative examples having no electrode under layer, favorable films were obtained from the example samples of the present invention.

TABLE 5

| | Sensing electrode part | $NO_2$(100 ppm) | |
|---|---|---|---|
| Material for electrode under layer | Material for sensing electrode | Initial sensitivity | Rate of change of drift |
| — | Pt—Rh (3 wt %) | 86 mV | +95% |
| — | $Cr_2O_3$ | 93 mV | +88% |
| — | $NiCr_2O_4$ | 89 mV | +86% |
| — | $FeCr_2O_4$ | 97 mV | +102% |
| — | $MgCr_2O_4$ | 95 mV | +83% |
| 15 mol % MgO—$ZrO_2$ | Pt—Rh (3 wt %) | 89 mV | +30% |
| 15 mol % MgO—$ZrO_2$ | $Cr_2O_3$ | 97 mV | +34% |
| 15 mol % MgO—$ZrO_2$ | $NiCr_2O_4$ | 100 mV | +40% |
| 15 mol % MgO—$ZrO_2$ | $FeCr_2O_4$ | 90 mV | +32% |
| 15 mol % MgO—$ZrO_2$ | $MgCr_2O_4$ | 86 mV | +38% |
| 12 mol % $CeO_2$—$ZrO_2$ | Pt—Rh (3 wt %) | 95 mV | +31% |

TABLE 4

| | Sensing electrode part | | $NO_2$(100 ppm) | |
|---|---|---|---|---|
| Material for solid electrolyte substrate | Material for electrode under layer | Material for sensing electrode | Initial sensitivity | Rate of change of drift |
| 6 mol % $Y_2O_3$—$ZrO_2$ | No under layer | Pt—Rh(3 wt %) | 84 mV | +98% |
| 6 mol % $Y_2O_3$—$ZrO_2$ | No under layer | $Cr_2O_3$ | 91 mV | +85% |
| 6 mol % $Y_2O_3$—$ZrO_2$ | No under layer | $NiCr_2O_4$ | 93 mV | +91% |
| 6 mol % $Y_2O_3$—$ZrO_2$ | 8 mol % $Y_2O_3$—$ZrO_2$ Pt— | Pt—Rh(3 wt %) | 95 mV | +94% |
| 6 mol % $Y_2O_3$—$ZrO_2$ | 8 mol % $Y_2O_3$—$ZrO_2$ Pt— | $Cr_2O_3$ | 100 mV | +90% |
| 6 mol % $Y_2O_3$—$ZrO_2$ | 8 mol % $Y_2O_3$—$ZrO_2$ Pt— | $NiCr_2O_4$ | 99 mV | +87% |
| 6 mol % $Y_2O_3$—$ZrO_2$ | 8 mol % $Y_2O_3$—$ZrO_2$ Pt 0.7 wt % | Pt—Rh(3 wt %) | 85 mV | +26% |
| 6 mol % $Y_2O_3$—$ZrO_2$ | 8 mol % $Y_2O_3$—$ZrO_2$ Pt 0.7 wt % | $Cr_2O_3$ | 90 mV | +30% |
| 6 mol % $Y_2O_3$—$ZrO_2$ | 8 mol % $Y_2O_3$—$ZrO_2$ Pt 0.7 wt % | $NiCr_2O_4$ | 95 mV | +22% |
| 12 mol % MgO—$ZrO_2$ | 8 mol % $Y_2O_3$—$ZrO_2$ Pt 0.7 wt % | Pt—Rh(3 wt %) | 83 mV | +31% |
| 12 mol % MgO—$ZrO_2$ | 8 mol % $Y_2O_3$—$ZrO_2$ Pt 0.7 wt % | $Cr_2O_3$ | 87 mV | +33% |
| 12 mol % MgO—$ZrO_2$ | 8 mol % $Y_2O_3$—$ZrO_2$ Pt 0.7 wt % | $NiCr_2O_4$ | 92 mV | +27% |

Example 4

NOx sensing devices having the structure of FIG. 1 were fabricated as in the example 1. Here, the electrode under layers and sensing electrodes were made of the materials shown in Table 5. Pt was added to all electrode under layer of the present example samples with the content of 0.7% by weight with respect to the total amount of the electrode under layer. The solid electrolyte substrates were zirconia solid electrolyte substrates containing 6-mol % yttria. The reference electrodes 7 were made of Pt. The obtained samples were evaluated for sensitivity characteristics and film conditions as in the example 1. To check the effects of the electrode under layers, samples having no electrode under layer were also prepared.

TABLE 5-continued

| | Sensing electrode part | $NO_2$(100 ppm) | |
|---|---|---|---|
| Material for electrode under layer | Material for sensing electrode | Initial sensitivity | Rate of change of drift |
| 12 mol % $CeO_2$—$ZrO_2$ | $Cr_2O_3$ | 93 mV | +30% |
| 12 mol % $CeO_2$—$ZrO_2$ | $NiCr_2O_4$ | 98 mV | +32% |
| 12 mol % $CeO_2$—$ZrO_2$ | $FeCr_2O_4$ | 90 mV | +36% |
| 12 mol % $CeO_2$—$ZrO_2$ | $MgCr_2O_4$ | 87 mV | +41% |
| 8 mol % $Y_2O_3$—$ZrO_2$ | Pt—Rh | 97 mV | +33% |

TABLE 5-continued

| | Sensing electrode part | NO$_2$(100 ppm) | |
|---|---|---|---|
| Material for electrode under layer | Material for sensing electrode | Initial sensitivity | Rate of change of drift |
| | (3 wt %) | | |
| 8 mol % Y$_2$O$_3$—ZrO$_2$ | Cr$_2$O$_3$ | 95 mV | +31% |
| 8 mol % Y$_2$O$_3$—ZrO$_2$ | NiCr$_2$O$_4$ | 96 mV | +30% |
| 8 mol % Y$_2$O$_3$—ZrO$_2$ | FeCr$_2$O$_4$ | 94 mV | +33% |
| 8 mol % Y$_2$O$_3$—ZrO$_2$ | MgCr$_2$O$_4$ | 89 mV | +35% |
| 15 mol % Sc$_2$O$_3$—ZrO$_2$ | Pt—Rh | 85 mV | +38% |
| | (3 wt %) | | |
| 15 mol % Sc$_2$O$_3$—ZrO$_2$ | Cr$_2$O$_3$ | 91 mV | +33% |
| 15 mol % Sc$_2$O$_3$—ZrO$_2$ | NiCr$_2$O$_4$ | 93 mV | +31% |
| 15 mol % Sc$_2$O$_3$—ZrO$_2$ | FeCr$_2$O$_4$ | 90 mV | +32% |
| 15 mol % Sc$_2$O$_3$—ZrO$_2$ | MgCr$_2$O$_4$ | 85 mV | +34% |
| 12 mol % Sc$_2$O$_3$-2 mol % CaO—ZrO$_2$ | Cr$_2$O$_3$ | 86 mV | +37% |
| 12 mol % Sc$_2$O$_3$-2 mol % CeO$_2$—ZrO$_2$ | Cr$_2$O$_3$ | 90 mV | +36% |
| 12 mol % CeO$_2$-2 mol % CaO—ZrO$_2$ | Cr$_2$O$_3$ | 91 mV | +41% |
| 12 mol % CeO$_2$-2 mol % MgO—ZrO$_2$ | Cr$_2$O$_3$ | 93 mV | +33% |
| 12 mol % CaO—ZrO$_2$ | Cr$_2$O$_3$ | 77 mV | +51% |
| 10 mol % ThO$_2$—ZrO$_2$ | Cr$_2$O$_3$ | 72 mV | +47% |
| 10 mol % Yb$_2$O$_3$—ZrO$_2$ | Cr$_2$O$_3$ | 68 mV | +56% |
| LaGaO$_3$ | Cr$_2$O$_3$ | 79 mV | +45% |
| LaGaO$_3$ | NiCr$_2$O$_4$ | 82 mV | +47% |

Example 5

NOx sensing devices having the structure of FIG. 1 were fabricated as in the example 1. Here, the sensing electrodes were made of Cr$_2$O$_3$ and the first precious metals or metal alloys shown in Table 6 were exclusively added to the sensing electrodes. The amount of addition was 50% by weight with respect to the sensing electrode. The electrode under layers were made of zirconia solid electrolyte containing the stabilizers shown in Table 6. Pt was added to the respective electrode under layers with the content of 0.7% by weight with respect to the total amount of the electrode under layer. The reference electrodes 7 were made of Pt. The obtained samples were evaluated for sensitivity characteristics and film conditions as in the example 1. To check the effects of the electrode under layers, samples having no electrode under layer were also prepared.

Table 6 shows the results. It is found that as compared to the conventional samples (comparative examples) having no electrode under layer, the electrodes of this example show little drop in initial sensitivity and can be obviously reduced in the rate of change of drift. As compared to Example 4, the electrodes of this example show a further reduction in drift. This suggests synergetic effect of the electrode under layer and the first precious metals added to the sensing electrode. Stereomicroscopic observations on the electrode films confirmed that favorable films were obtained in the same way as Example 4.

TABLE 6

| | Sensing electrode part | NO$_2$(100 ppm) | |
|---|---|---|---|
| Material for electrode under layer | Material for first precious metal added to sensing electrode | Initial sensitivity | Rate of change of drift |
| — | Au | 96 mV | +85% |
| — | Ir | 92 mV | +92% |
| — | Rh | 97 mV | +83% |
| — | Au—Ir(5 wt %) | 95 mV | +89% |
| — | Ir—Rh(5 wt %) | 92 mV | +105% |
| — | Au—Rh(5 wt %) | 96 mV | +94% |
| 12 mol % CeO$_2$—ZrO$_2$ | Au | 90 mV | +30% |
| 12 mol % CeO$_2$—ZrO$_2$ | Ir | 92 mV | +27% |
| 12 mol % CeO$_2$—ZrO$_2$ | Rh | 90 mV | +25% |
| 12 mol % CeO$_2$—ZrO$_2$ | Au—Ir(5 wt %) | 92 mV | +24% |
| 12 mol % CeO$_2$—ZrO$_2$ | Ir—Rh(5 wt %) | 85 mV | +28% |
| 12 mol % CeO$_2$—ZrO$_2$ | Au—Rh(5 wt %) | 90 mV | +29% |
| 13 mol % MgO—ZrO$_2$ | Au | 88 mV | +32% |
| 13 mol % MgO—ZrO$_2$ | Ir | 90 mV | +25% |
| 13 mol % MgO—ZrO$_2$ | Rh | 89 mV | +26% |
| 13 mol % MgO—ZrO$_2$ | Au—Ir(5 wt %) | 92 mV | +21% |
| 13 mol % MgO—ZrO$_2$ | Ir—Rh(5 wt %) | 93 mV | +27% |
| 13 mol % MgO—ZrO$_2$ | Au—Rh(5 wt %) | 88 mV | +25% |
| 15 mol % Sc$_2$O$_3$—ZrO$_2$ | Au | 93 mV | +26% |
| 15 mol % Sc$_2$O$_3$—ZrO$_2$ | Ir | 95 mV | +24% |
| 15 mol % Sc$_2$O$_3$—ZrO$_2$ | Rh | 91 mV | +28% |
| 15 mol % Sc$_2$O$_3$—ZrO$_2$ | Au—Ir(5 wt %) | 85 mV | +22% |
| 15 mol % Sc$_2$O$_3$—ZrO$_2$ | Ir—Rh(5 wt %) | 93 mV | +28% |
| 15 mol % Sc$_2$O$_3$—ZrO$_2$ | Au—Rh(5 wt %) | 87 mV | +28% |
| 8 mol % Y$_2$O$_3$—ZrO$_2$ | Au | 92 mV | +25% |
| 8 mol % Y$_2$O$_3$—ZrO$_2$ | Ir | 91 mV | +22% |
| 8 mol % Y$_2$O$_3$—ZrO$_2$ | Rh | 89 mV | +27% |
| 8 mol % Y$_2$O$_3$—ZrO$_2$ | Au—Ir(5 wt %) | 87 mV | +25% |
| 8 mol % Y$_2$O$_3$—ZrO$_2$ | Ir—Rh(5 wt %) | 92 mV | +26% |
| 8 mol % Y$_2$O$_3$—ZrO$_2$ | Au—Rh(5 wt %) | 89 mV | +27% |

Example 6

NOx sensing devices having the structure of FIG. 1 were fabricated as in the example 1. Here, the sensing electrodes were made of Cr$_2$O$_3$ and the second precious metals or metal alloys shown in Table 7 were exclusively added to the sensing electrodes. The amount of addition was 0.5% by weight with respect to the sensing electrode. The electrode under layers were made of zirconia solid electrolyte containing the stabilizers shown in Table 7. Pt was added to the respective electrode base layers with the content of 0.7% by weight with respect to the total amount of the electrode under layer. The reference electrodes 7 were made of Pt. The obtained samples were evaluated for sensitivity characteristics and film conditions as in the example 1. To check the effects of the electrode under layers, samples having no electrode under layer were also prepared.

Table 7 shows the results. It is found that as compared to the conventional samples (comparative examples) having no electrode under layer, the electrodes of this example show little drop in initial sensitivity and can be obviously reduced in the rate of change of drift. As compared to Example 4, the electrodes of the present example samples show a further reduction in drift. This suggests synergetic effect of the electrode under layer and the second precious metals added to the sensing electrode. Stereomicroscopic observations on the electrode films confirmed that favorable films were obtained in the same way as Example 4.

TABLE 7

| Sensing electrode part | | NO$_2$(100 ppm) | |
|---|---|---|---|
| Material for electrode under layer | Material for second precious metal added to sensing electrode | Initial sensitivity | Rate of change of drift |
| — | Pt | 93 mV | +103% |
| — | Pd | 91 mV | +91% |
| — | Ru | 93 mV | +92% |
| — | Pt—Pd(30 wt %) | 89 mV | +94% |
| — | Pd—Ru(20 wt %) | 92 mV | +86% |
| — | Pt—Ru(20 wt %) | 88 mV | +90% |
| 12 mol % CeO$_2$—ZrO$_2$ | Pt | 92 mV | +24% |
| 12 mol % CeO$_2$—ZrO$_2$ | Pd | 90 mV | +30% |
| 12 mol % CeO$_2$—ZrO$_2$ | Ru | 88 mV | +24% |
| 12 mol % CeO$_2$—ZrO$_2$ | Pt—Pd(30 wt %) | 96 mV | +23% |
| 12 mol % CeO$_2$—ZrO$_2$ | Pd—Ru(20 wt %) | 91 mV | +21% |
| 12 mol % CeO$_2$—ZrO$_2$ | Pt—Ru(20 wt %) | 90 mV | +29% |
| 13 mol % MgO—ZrO$_2$ | Pt | 91 mV | +21% |
| 13 mol % MgO—ZrO$_2$ | Pd | 93 mV | +23% |
| 13 mol % MgO—ZrO$_2$ | Ru | 91 mV | +26% |
| 13 mol % MgO—ZrO$_2$ | Pt—Pd(30 wt %) | 86 mV | +24% |
| 13 mol % MgO—ZrO$_2$ | Pd—Ru(20 wt %) | 94 mV | +26% |
| 13 mol % MgO—ZrO$_2$ | Pt—Ru(20 wt %) | 91 mV | +23% |
| 15 mol % Sc$_2$O$_3$—ZrO$_2$ | Pt | 89 mV | +29% |
| 15 mol % Sc$_2$O$_3$—ZrO$_2$ | Pd | 92 mV | +22% |
| 15 mol % Sc$_2$O$_3$—ZrO$_2$ | Ru | 91 mV | +26% |
| 15 mol % Sc$_2$O$_3$—ZrO$_2$ | Pt—Pd(30 wt %) | 95 mV | +30% |
| 15 mol % Sc$_2$O$_3$—ZrO$_2$ | Pd—Ru(20 wt %) | 88 mV | +22% |
| 15 mol % Sc$_2$O$_3$—ZrO$_2$ | Pt—Ru(20 wt %) | 92 mV | +23% |
| 8 mol % Y$_2$O$_3$—ZrO$_2$ | Pt | 87 mV | +25% |
| 8 mol % Y$_2$O$_3$—ZrO$_2$ | Pd | 90 mV | +23% |
| 8 mol % Y$_2$O$_3$—ZrO$_2$ | Ru | 88 mV | +24% |
| 8 mol % Y$_2$O$_3$—ZrO$_2$ | Pt—Pd(30 wt %) | 93 mV | +28% |
| 8 mol % Y$_2$O$_3$—ZrO$_2$ | Pd—Ru(20 wt %) | 89 mV | +20% |
| 8 mol % Y$_2$O$_3$—ZrO$_2$ | Pt—Ru(20 wt %) | 91 mV | +22% |

Example 7

NOx sensing devices having the structure of FIG. 1 were fabricated as in the example 1. Here, Cr$_2$O$_3$ was used as metal oxide for the sensing electrode. The first precious metals shown in Table 8 were added to the sensing electrodes with the amount of 50% by weight. Further, the second precious metals shown in Table 8 were also added to the sensing electrode with the amount of 0.5% by weight. The electrode under layers were made of zirconia solid electrolyte containing the stabilizers shown in Table 8. Pt was added to the respective electrode under layers with the amount of 0.7% by weight with respect to the total amount of the electrode under layer. The reference electrodes 7 were made of Pt. The obtained samples were evaluated for sensitivity characteristics and film conditions as in the example 1. To check the effects of the electrode under layers, samples having no electrode under layer were also prepared.

Table 8 shows the results. It is found that as compared to the conventional samples (comparative examples) having no electrode under layer, the electrodes of this example show little drop in initial sensitivity and can be obviously reduced in the rate of change of drift. As compared to Examples 6 and 7, the electrodes of the present example samples show a further reduction in drift. These results confirms that both the first and second precious metal can be added to further improve the electrode stability. Stereomicroscopic observations on the electrode films confirmed that favorable films were obtained in the same way as Example 4.

TABLE 8

| | Sensing electrode part | | | | | |
|---|---|---|---|---|---|---|
| | Material for first precious metal | | Material for second precious metal | | NO$_2$(100 ppm) | |
| Material for electrode under layer | added to sensing electrode | Amount of addition | added to sensing electrode | Amount of addition | Initial sensitivity | Rate of change of drift |
| 12 mol % CeO$_2$—ZrO$_2$ | Au | 50 wt % | Pt | 0.5 wt % | 91 mV | +15% |
| 12 mol % CeO$_2$—ZrO$_2$ | Au | 50 wt % | Pd | 0.5 wt % | 90 mV | +21% |
| 12 mol % CeO$_2$—ZrO$_2$ | Au | 50 wt % | Ru | 0.5 wt % | 87 mV | +16% |
| 12 mol % CeO$_2$—ZrO$_2$ | Ir | 50 wt % | Pt | 0.5 wt % | 91 mV | +14% |
| 12 mol % CeO$_2$—ZrO$_2$ | Ir | 50 wt % | Pd | 0.5 wt % | 85 mV | +16% |
| 12 mol % CeO$_2$—ZrO$_2$ | Ir | 50 wt % | Ru | 0.5 wt % | 93 mV | +18% |
| 12 mol % CeO$_2$—ZrO$_2$ | Ru | 50 wt % | Pt | 0.5 wt % | 88 mV | +17% |
| 12 mol % CeO$_2$—ZrO$_2$ | Ru | 50 wt % | Pd | 0.5 wt % | 87 mV | +20% |
| 12 mol % CeO$_2$—ZrO$_2$ | Ru | 50 wt % | Ru | 0.5 wt % | 85 mV | +16% |
| 13 mol % MgO—ZrO$_2$ | Au | 50 wt % | Pt | 0.5 wt % | 89 mV | +12% |
| 13 mol % MgO—ZrO$_2$ | Au | 50 wt % | Pd | 0.5 wt % | 85 mV | +17% |
| 13 mol % MgO—ZrO$_2$ | Au | 50 wt % | Ru | 0.5 wt % | 89 mV | +14% |
| 13 mol % MgO—ZrO$_2$ | Ir | 50 wt % | Pt | 0.5 wt % | 90 mV | +15% |
| 13 mol % MgO—ZrO$_2$ | Ir | 50 wt % | Pd | 0.5 wt % | 90 mV | +20% |
| 13 mol % MgO—ZrO$_2$ | Ir | 50 wt % | Ru | 0.5 wt % | 86 mV | +16% |
| 13 mol % MgO—ZrO$_2$ | Ru | 50 wt % | Pt | 0.5 wt % | 89 mV | +18% |
| 13 mol % MgO—ZrO$_2$ | Ru | 50 wt % | Pd | 0.5 wt % | 92 mV | +14% |
| 13 mol % MgO—ZrO$_2$ | Ru | 50 wt % | Ru | 0.5 wt % | 91 mV | +16% |
| 15 mol % Sc$_2$O$_3$—ZrO$_2$ | Au | 50 wt % | Pt | 0.5 wt % | 90 mV | +11% |
| 15 mol % Sc$_2$O$_3$—ZrO$_2$ | Au | 50 wt % | Pd | 0.5 wt % | 91 mV | +16% |
| 15 mol % Sc$_2$O$_3$—ZrO$_2$ | Au | 50 wt % | Ru | 0.5 wt % | 85 mV | +15% |

TABLE 8-continued

<table>
<tr><td colspan="7">Sensing electrode part</td></tr>
<tr><td rowspan="3">Material for electrode under layer</td><td>Material for first precious metal added to sensing electrode</td><td>Amount of addition</td><td>Material for second precious metal added to sensing electrode</td><td>Amount of addition</td><td colspan="2">NO$_2$(100 ppm)</td></tr>
<tr><td></td><td></td><td></td><td></td><td>Initial sensitivity</td><td>Rate of change of drift</td></tr>
<tr><td></td><td></td><td></td><td></td><td></td><td></td></tr>
<tr><td>15 mol % Sc$_2$O$_3$—ZrO$_2$</td><td>Ir</td><td>50 wt %</td><td>Pt</td><td>0.5 wt %</td><td>93 mV</td><td>+17%</td></tr>
<tr><td>15 mol % Sc$_2$O$_3$—ZrO$_2$</td><td>Ir</td><td>50 wt %</td><td>Pd</td><td>0.5 wt %</td><td>90 mV</td><td>+15%</td></tr>
<tr><td>15 mol % Sc$_2$O$_3$—ZrO$_2$</td><td>Ir</td><td>50 wt %</td><td>Ru</td><td>0.5 wt %</td><td>89 mV</td><td>+20%</td></tr>
<tr><td>15 mol % Sc$_2$O$_3$—ZrO$_2$</td><td>Ru</td><td>50 wt %</td><td>Pt</td><td>0.5 wt %</td><td>91 mV</td><td>+13%</td></tr>
<tr><td>15 mol % Sc$_2$O$_3$—ZrO$_2$</td><td>Ru</td><td>50 wt %</td><td>Pd</td><td>0.5 wt %</td><td>93 mV</td><td>+16%</td></tr>
<tr><td>15 mol % Sc$_2$O$_3$—ZrO$_2$</td><td>Ru</td><td>50 wt %</td><td>Ru</td><td>0.5 wt %</td><td>91 mV</td><td>+17%</td></tr>
<tr><td>8 mol % Y$_2$O$_3$—ZrO$_2$</td><td>Au</td><td>50 wt %</td><td>Pt</td><td>0.5 wt %</td><td>93 mV</td><td>+13%</td></tr>
<tr><td>8 mol % Y$_2$O$_3$—ZrO$_2$</td><td>Au</td><td>50 wt %</td><td>Pd</td><td>0.5 wt %</td><td>90 mV</td><td>+12%</td></tr>
<tr><td>8 mol % Y$_2$O$_3$—ZrO$_2$</td><td>Au</td><td>50 wt %</td><td>Ru</td><td>0.5 wt %</td><td>88 mV</td><td>+14%</td></tr>
<tr><td>8 mol % Y$_2$O$_3$—ZrO$_2$</td><td>Ir</td><td>50 wt %</td><td>Pt</td><td>0.5 wt %</td><td>90 mV</td><td>+15%</td></tr>
<tr><td>8 mol % Y$_2$O$_3$—ZrO$_2$</td><td>Ir</td><td>50 wt %</td><td>Pd</td><td>0.5 wt %</td><td>92 mV</td><td>+17%</td></tr>
<tr><td>8 mol % Y$_2$O$_3$—ZrO$_2$</td><td>Ir</td><td>50 wt %</td><td>Ru</td><td>0.5 wt %</td><td>87 mV</td><td>+19%</td></tr>
<tr><td>8 mol % Y$_2$O$_3$—ZrO$_2$</td><td>Ru</td><td>50 wt %</td><td>Pt</td><td>0.5 wt %</td><td>88 mV</td><td>+13%</td></tr>
<tr><td>8 mol % Y$_2$O$_3$—ZrO$_2$</td><td>Ru</td><td>50 wt %</td><td>Pd</td><td>0.5 wt %</td><td>90 mV</td><td>+14%</td></tr>
<tr><td>8 mol % Y$_2$O$_3$—ZrO$_2$</td><td>Ru</td><td>50 wt %</td><td>Ru</td><td>0.5 wt %</td><td>89 mV</td><td>+15%</td></tr>
</table>

Example 8

NOx sensors (gas sensing devices) of the present invention having the structure of FIG. 1 were fabricated. In the present example, Cr$_2$O$_3$ was used as a metal oxide for the sensing electrodes. The electrode under layers 15 were made of zirconia solid electrolytes containing 12-mol % CeO$_2$, 15-mol % Sc$_2$O$_3$, 13-mol % MgO, and 10-mol % Y$_2$O$_3$, respectively. As the first precious metal, Au was added to these electrode under layers 15 with different amounts in the range of 0–30% by weight. Specifically, the amounts of addition were on the orders of 0%, 0.5%, 1%, 5%, 10%, 20%, and 30% by weight, respectively. In addition to the Au-added zirconia base layer containing 12-mol % CeO$_2$, Ir- and Rh-added samples were also prepared. Here, no second precious metal was added. In the present example, the reference electrodes were also made of Pt. The fabrication method of these samples was the same as that of the example 1.

Figure 9:
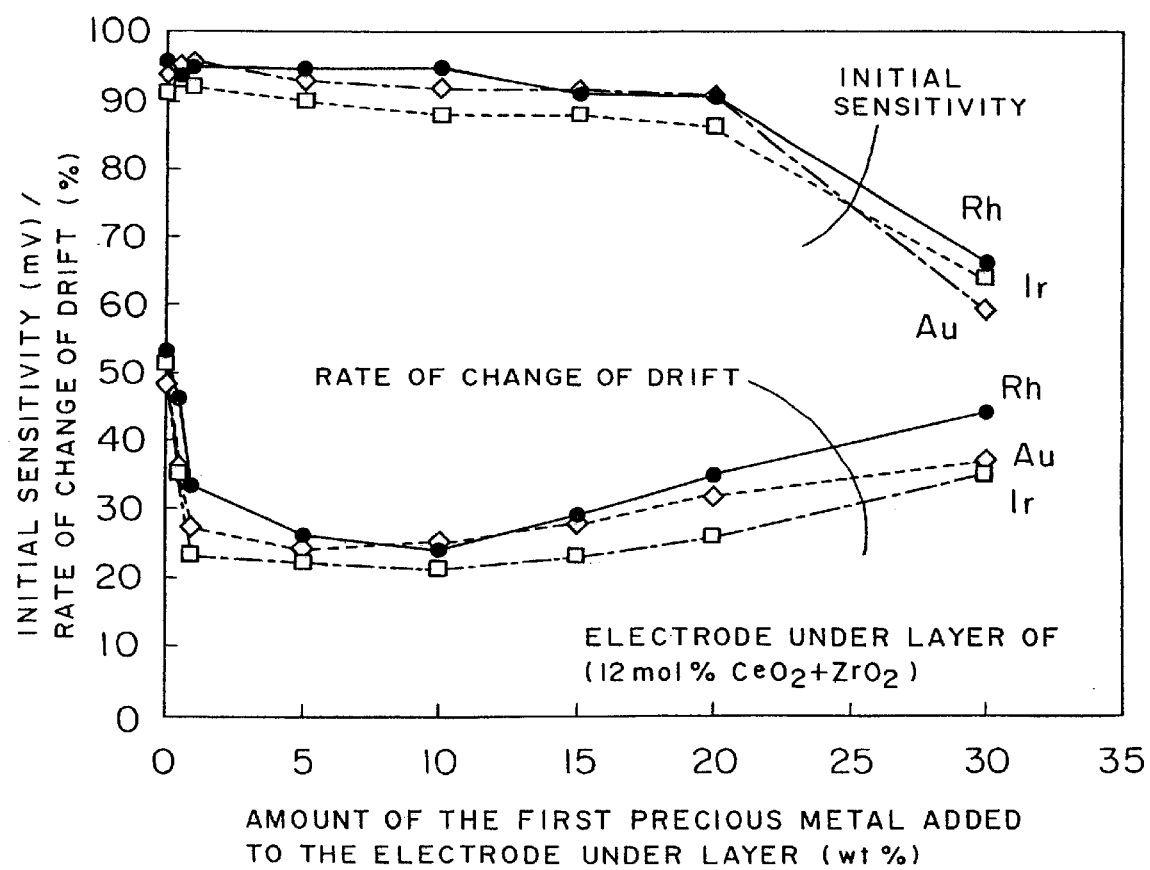
FIG. 9 shows initial sensitivity and rate of change of drift as a function of amount of the precious metal added to the electrode under layer.
Figure 10:
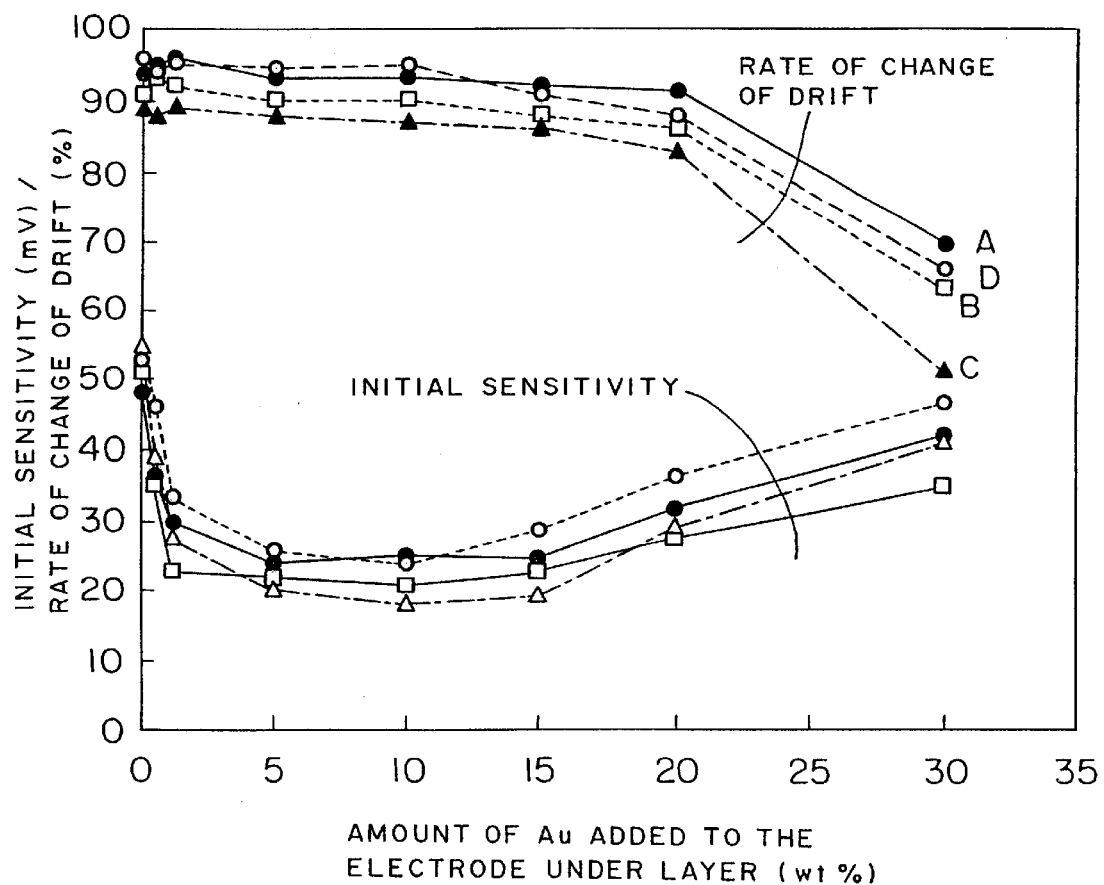
FIG. 10 shows initial sensitivity and rate of change of drift as a function of amount of Au added to the electrode under layer.

Like the example 1, the sensor samples prepared thus were put in an electric furnace and evaluated for sensitivity characteristics to NO$_2$ (100 ppm). The sensitivity characteristics examined were initial sensitivity and the rate of change of sensitivity (the rate of change of drift) under a predetermined accelerate condition. FIG. 9 shows the results of evaluations as to the dependence on the amounts of addition of the respective precious metals, with 12-mol % CeO$_2$—ZrO$_2$ as the electrode under layers 15. FIG. 10 shows the results of evaluations as to the dependence of electrode under layers 15, made of zirconia solid electrolytes with various stabilizers, on the amount of Au which is added as the first precious metal. In FIG. 10, the symbols A, B, C, and D represent the samples that are made of zirconia solid electrolytes containing 12-mol % CeO$_2$, 15-mol % Sc$_2$O$_3$, 13-mol % MgO, and 10-mol % Y$_2$O$_3$, respectively.

These results confirms that in each sample, the first precious metal of 0.1–30% by weight can be added to reduce the rate of change of drift greatly without detriment to the sensitivity characteristics. The results also show that a range of 0.5–30% by weight is preferable, and a range of 1–20% by weight is yet preferable.

Example 9

NOx sensors (gas sensing devices) of the present invention having the structure of FIG. 1 were fabricated. In the present example, Cr$_2$O$_3$ was used as a metal oxide for the sensing electrodes. The electrode under layers 15 were made of zirconia solid electrolytes containing 12-mol % CeO$_2$, 15-mol % Sc$_2$O$_3$, 13-mol % MgO, and 10-mol % Y$_2$O$_3$, respectively. As the second precious metal, Pt was added to these electrode under layers 15 with different amounts in the range of 0–5% by weight. Specifically, the amounts of addition were on the orders of 0%, 0.05%, 0.1%, 0.5%, 1%, 2%, 3%, 4%, and 5% by weight, respectively. In addition to the Pt-added zirconia under layer containing 12-mol % CeO$_2$, Pd- and Ru-added samples were also prepared. Here, no first precious metal was added. In the present example, the reference electrodes were also made of Pt. The fabrication method of these samples was the same as that of the example 1.

Figure 11:
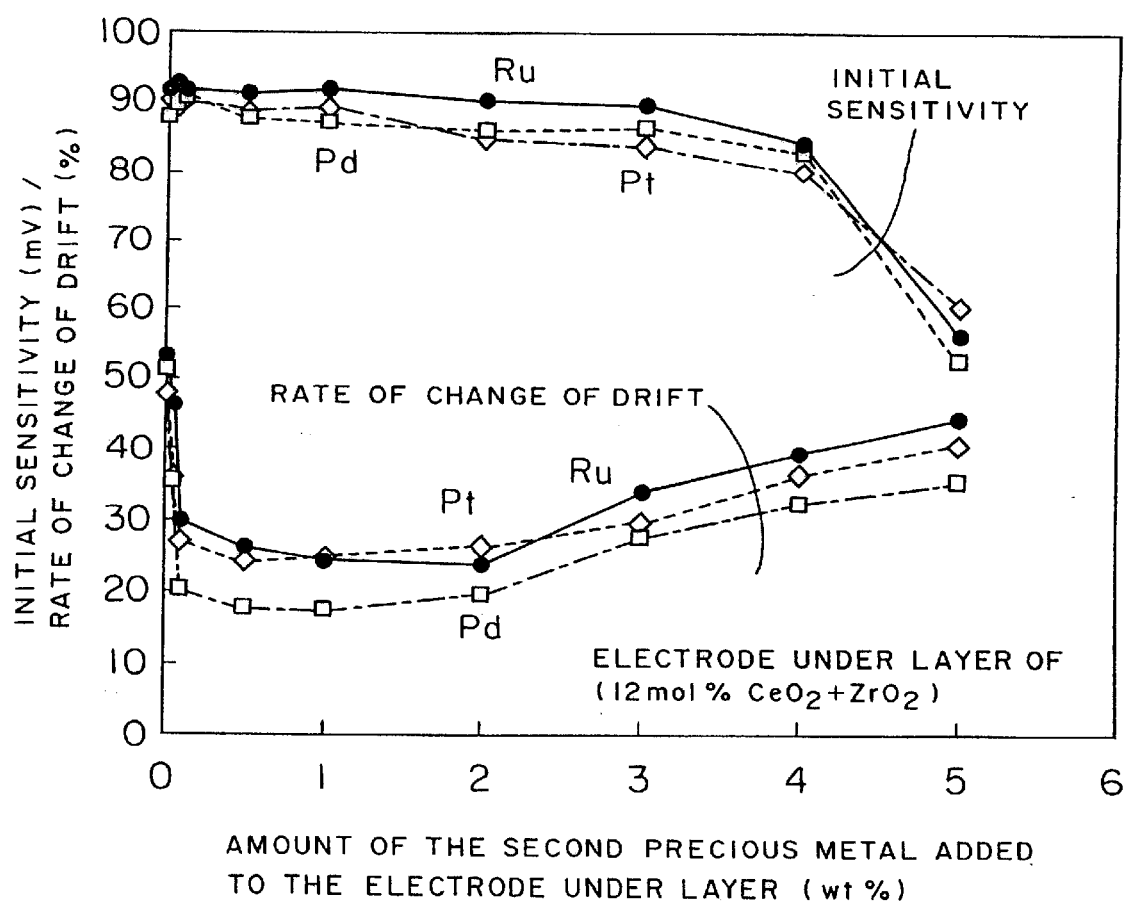
FIG. 11 shows initial sensitivity and rate of change of drift as a function of amount of the precious metal added to the electrode under layer.
Figure 12:
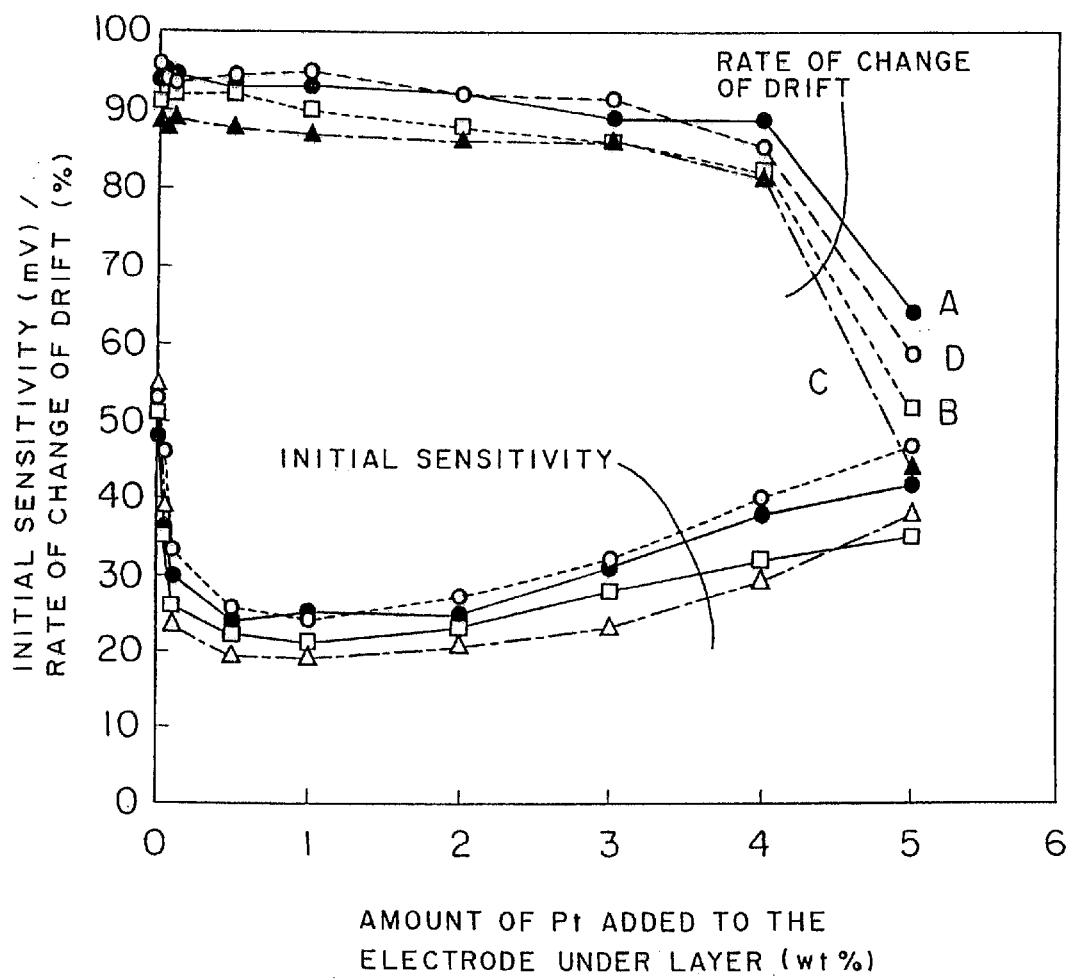
FIG. 12 shows initial sensitivity and rate of change of drift as a function of amount of Pt added to the electrode under layer.

Like example 1, the sensor samples prepared thus were evaluated for sensitivity characteristics to NO$_2$ (100 ppm). FIG. 11 shows the results of evaluations as to the dependence on the amounts of addition of the respective precious metals, with 12-mol % CeO$_2$—ZrO$_2$ as the electrode under layers 15. FIG. 12 shows the results of evaluations as to the dependence of electrode under layers 15, made of zirconia solid electrolytes with various stabilizers, on the amount of Pt which is added as the second precious metal. In FIG. 12, the symbols A, B, C, and D represent the samples that are made of zirconia solid electrolytes containing 12-mol % CeO$_2$, 15-mol % Sc$_2$O$_3$, 13-mol % MgO, and 10-mol % Y$_2$O$_3$, respectively.

These results confirms that in each sample, the second precious metal of 0.05–4% by weight can be added to reduce the rate of change of drift greatly without detriment to the sensitivity characteristics. The results also show that a range of 0.1–2% by weight is preferable.

Example 10

NOx sensors (gas sensing devices) of the present invention having the structure of FIG. 1 were fabricated. In the present example, $NiCr_2O_4$ was used as a metal oxide for the sensing electrodes. The electrode under layers 15 were made of zirconia solid electrolytes containing 12-mol % $CeO_2$, 15-mol % $Sc_2O_3$, 13-mol % MgO, and 10-mol % $Y_2O_3$, respectively. As the second precious metal, Pt was added to these electrode under layers 15 with the amount of 1.0% by weight. Further, as the first precious metal, Au was added to these electrode under layers with different amounts in the range of 0–40% by weight. Specifically, the amounts of addition were on the orders of 0%, 0.5%, 1%, 5%, 10%, 20%, 30%, and 40% by weight, respectively. In addition to the Au-added zirconia under layer containing 12-mol % $CeO_2$, Ir- and Rh-added samples were also prepared. In the present example, the reference electrodes were also made of Pt. The fabrication method of these samples was the same as that of the example 1.

Figure 13:
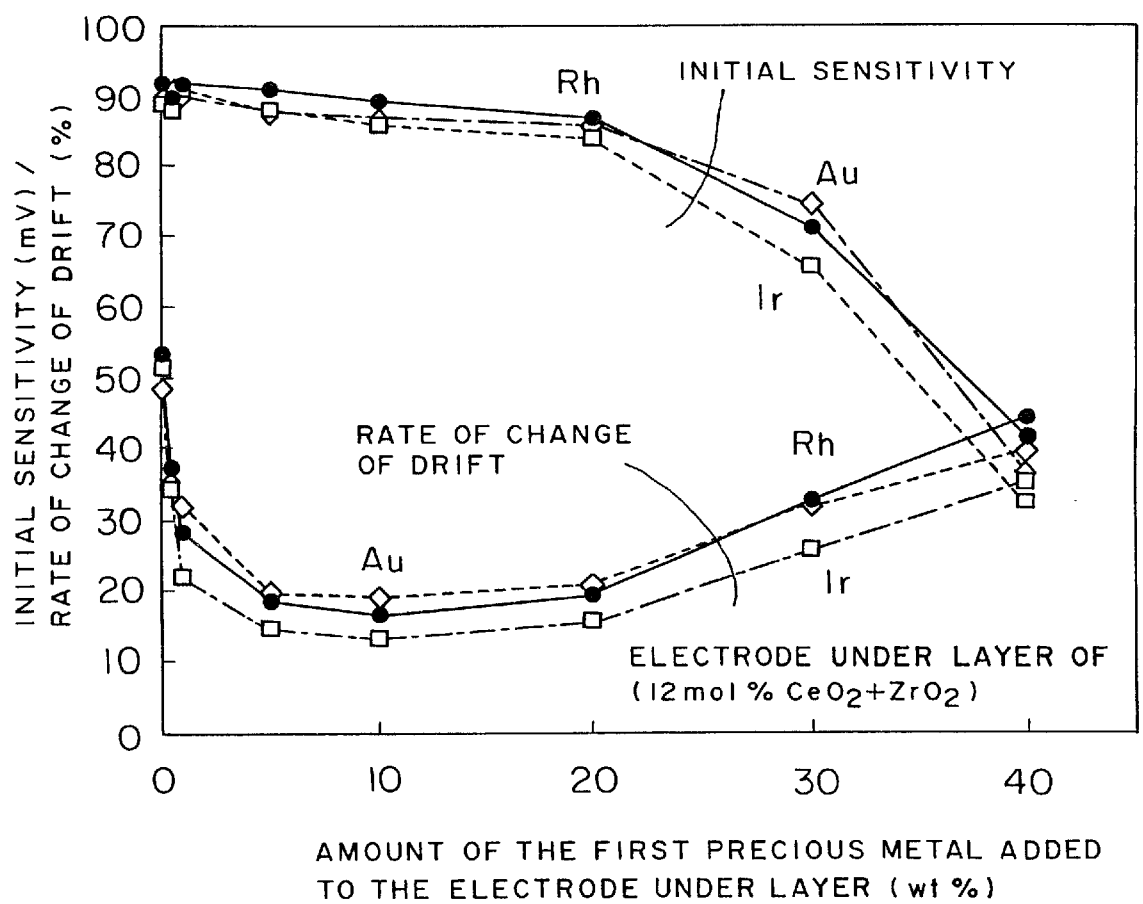
FIG. 13 shows initial sensitivity and rate of change of drift as a function of amount of the first precious metal added to the electrode under layer.
Figure 14:
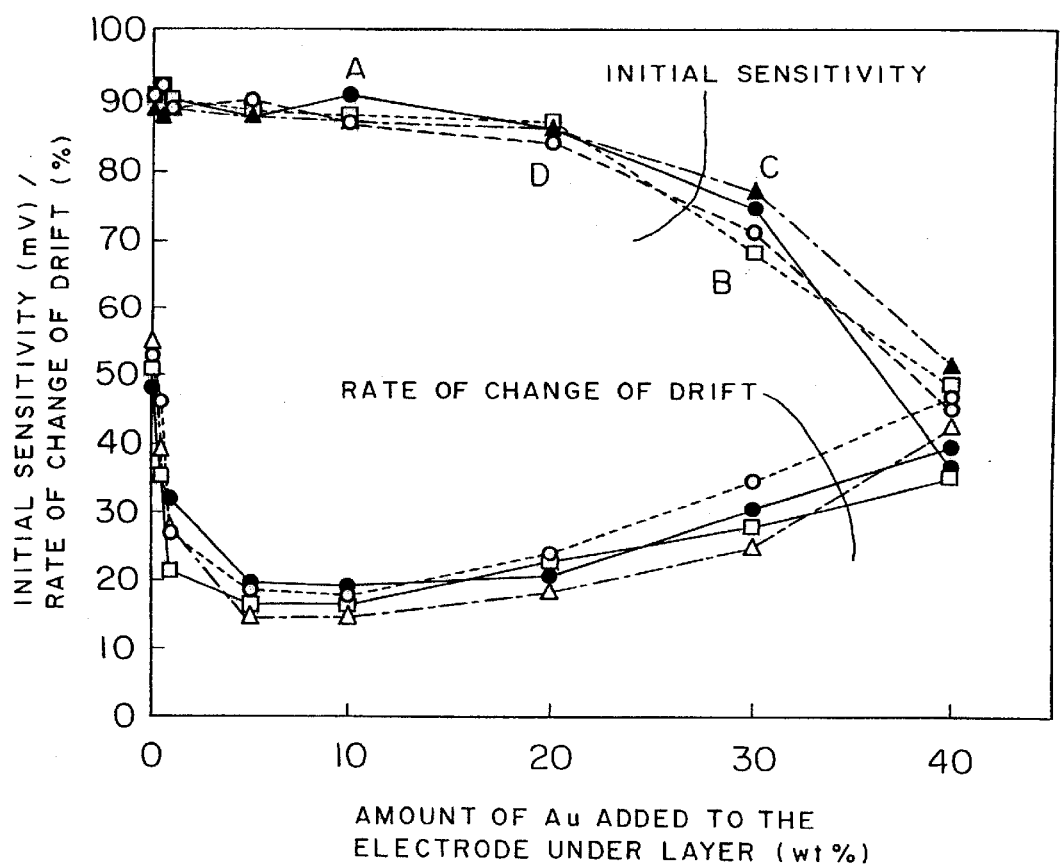
FIG. 14 shows initial sensitivity and rate of change of drift as a function of amount of Au added to the electrode under layer.

Like example 1, the sensor samples prepared thus were evaluated for sensitivity characteristics to $NO_2$ (100 ppm). FIG. 11 shows the results of evaluations as to the dependence on the amounts of addition of the respective precious metals, with 12-mol % $CeO_2$—$ZrO_2$ as the electrode under layers 15. FIG. 13 shows the results of evaluations as to the dependence of electrode under layers 15, made of 12-mol % $CeO_2$—$ZrO_2$ on the amount of various metals which is added as the first precious metal. FIG. 14 shows the results of evaluations as to the dependence of electrode under layers 15, made of zirconia solid electrolytes with various stabilizers, on the amount of Au which is added as the first precious metal. In FIG. 14, the symbols A, B, C, and D represent the samples that are made of zirconia solid electrolytes containing 12-mol % $CeO_2$, 15-mol % $Sc_2O_3$, 13-mol % MgO, and 10-mol % $Y_2O_3$, respectively.

These results confirm that in case that the second precious metal was added to the electrode under layer, the first precious metal of 0.1–30% by weight can be added to reduce the rate of change of drift greatly without detriment to the sensitivity characteristics. The results also show that a range of 0.1–20% by weight is preferable, and a range of 1–15% by weight is yet preferable.

Example 11

NOx sensors (gas sensing devices) of the present invention having the structure of FIG. 1 were fabricated. In the present example, $Cr_2O_3$ was used as a metal oxide for the sensing electrodes. As the first precious metal, Au or Ir was added to these sensing electrodes with different amounts in the range of 0–90% by weight at intervals of 10% by weight. Here, no second precious metal was added to the sensing electrode. The electrode under layers 15 were made of zirconia solid electrolytes containing 12-mol % $CeO_2$ or 15-mol % $Sc_2O_3$. As the second precious metal, Pt was added to these electrode under layers 15 with the amount of 0.7% by weight. In the present example, the reference electrodes were also made of Pt. The fabrication method of these samples was the same as that of the example 1.

Figure 15:
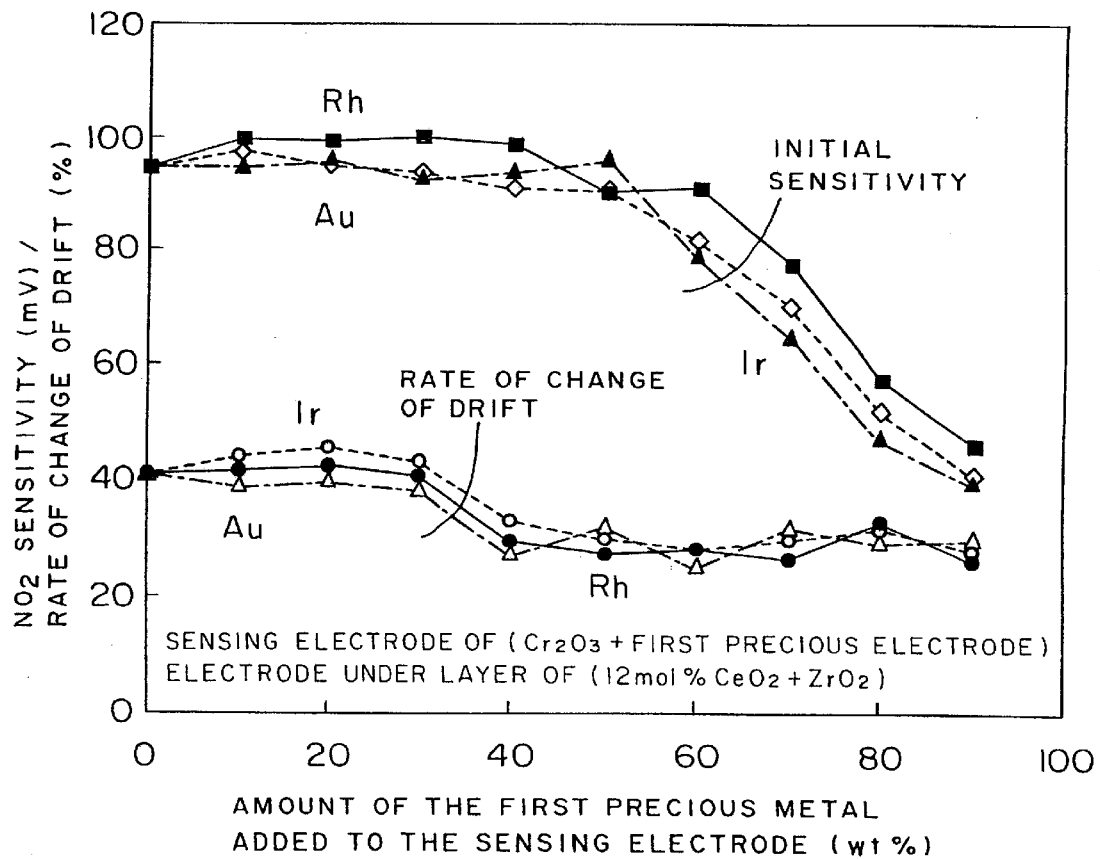
FIG. 15 shows initial $NO_2$ sensitivity and rate of change of drift as a function of amount of the first precious metal added to the sensing electrode.
Figure 16:
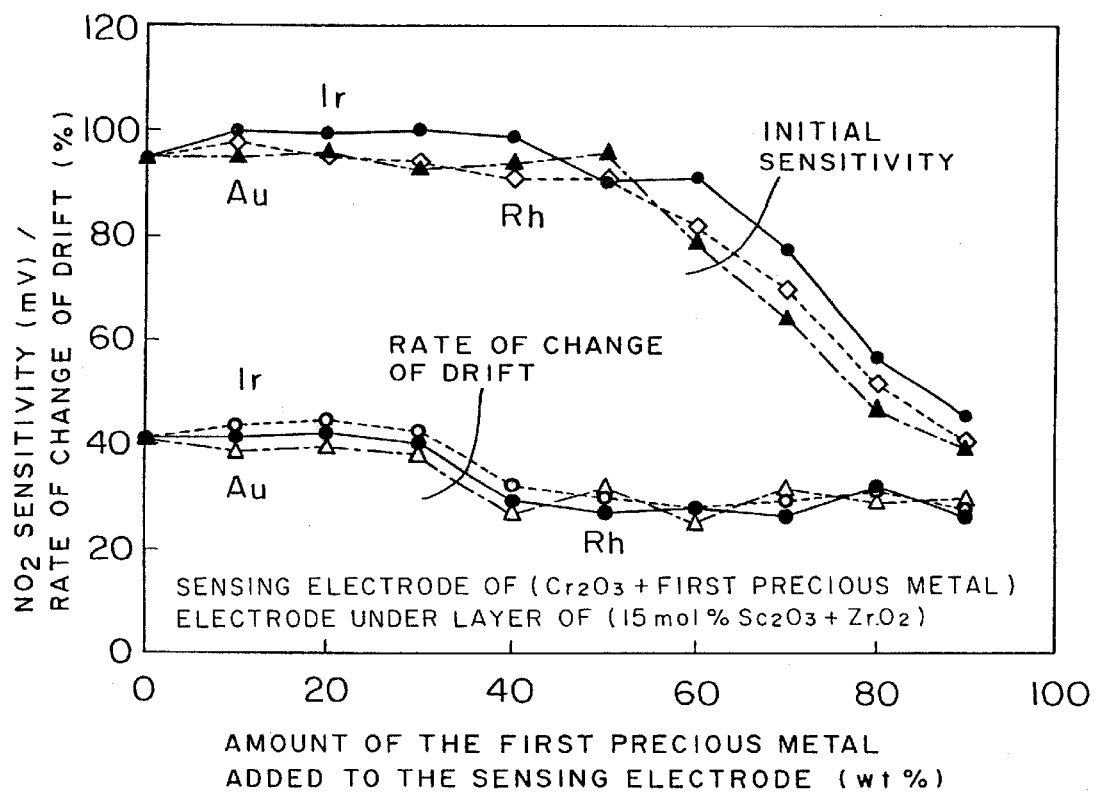
FIG. 16 shows initial $NO_2$ sensitivity and rate of change of drift as a function of amount of the first precious metal added to the sensing electrode.

Like example 1, the sensor samples prepared thus were evaluated for sensitivity characteristics to $NO_2$ (100 ppm). FIGS. 15 and 16 show the results of evaluations in case that the electrode under layers 15 were made of zirconia solid electrolytes containing 12-mol % $CeO_2$ or 15-mol % $Sc_2O_3$, respectively.

These results also confirm that the first precious metal of 40–70% by weight can be added to the sensing electrode of metal oxide to reduce the rate of change of drift greatly without detriment to the sensitivity characteristics. The results also show that a range of 40–60% by weight is preferable.

Example 12

NOx sensors (gas sensing devices) of the present invention having the structure of FIG. 1 were fabricated. In the present example, $Cr_2O_3$ was used as a metal oxide for the sensing electrodes. As the second precious metal, Pt or Pd was added to these sensing electrodes with different amounts in the range of 0–7% by weight. Specifically, the amounts of addition were on the orders of 0%, 0.05%, 0.1%, 0.5%, 1%, 2%, 3% 5%, and 7% by weight, respectively. Here, no first precious metal was added to the sensing electrode. The electrode under layers 15 were made of zirconia solid electrolytes containing 12-mol % $CeO_2$ or 15-mol % $Sc_2O_3$. As the second precious metal, Pt was added to these electrode base layers 15 with the amount of 0.7% by weight. In the present example, the reference electrodes were also made of Pt. The fabrication method of these samples was the same as that of the example 1.

Figure 17:
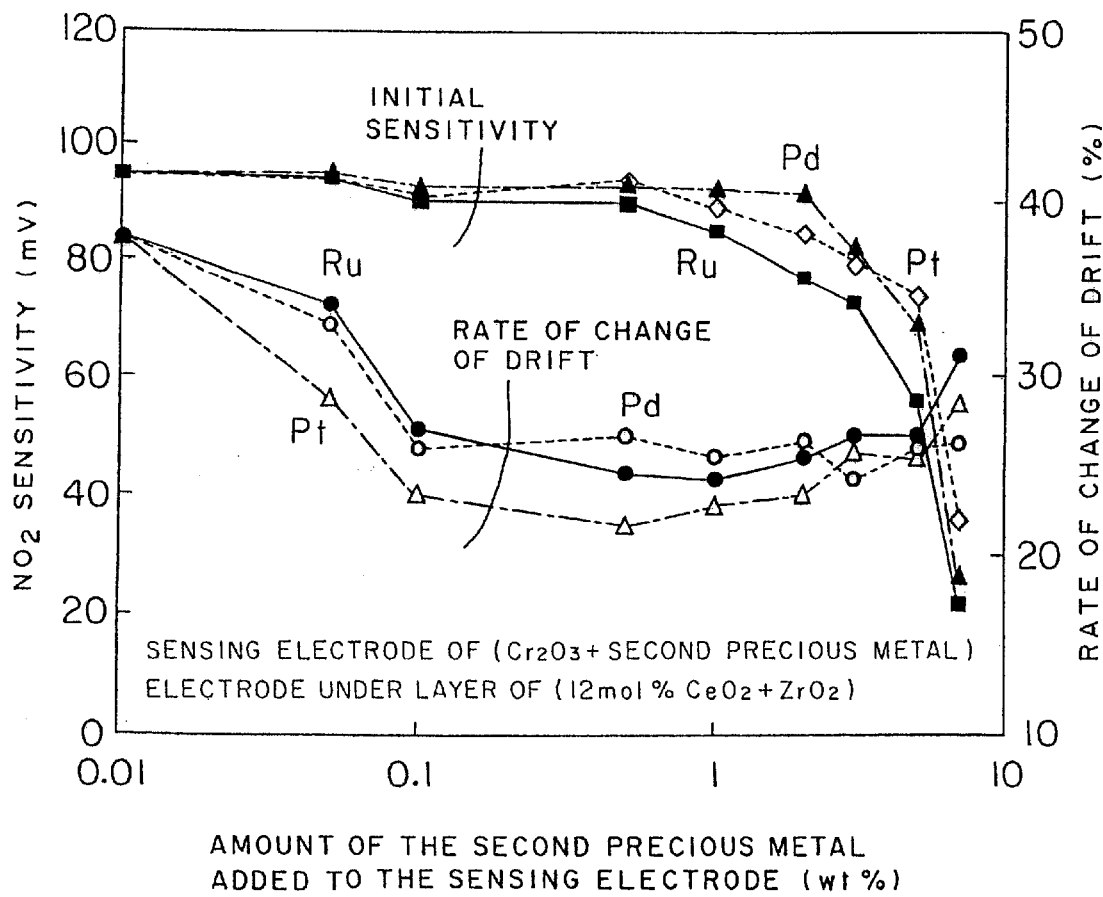
FIG. 17 shows initial $NO_2$ sensitivity and rate of change of drift as a function of amount of the second precious metal added to the sensing electrode.
Figure 18:
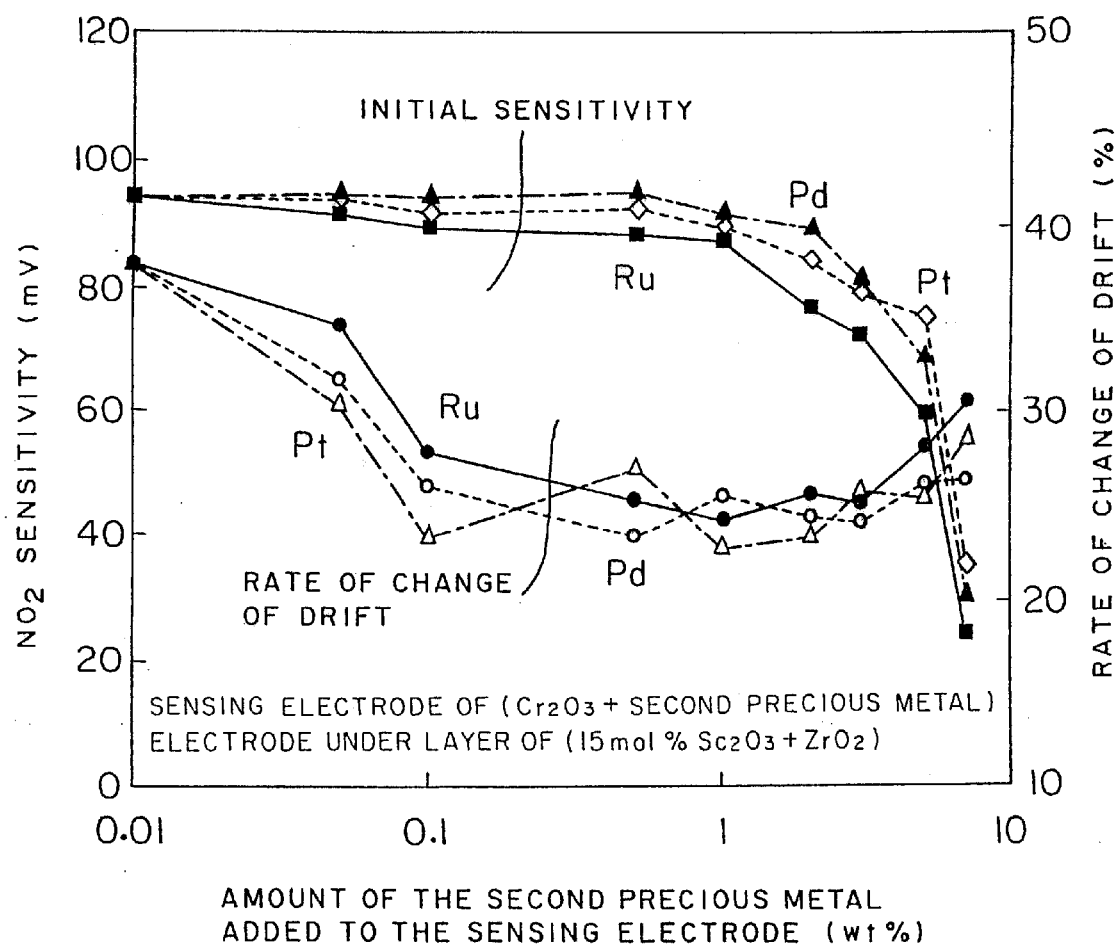
FIG. 18 shows initial $NO_2$ sensitivity and rate of change of drift as a function of amount of the second precious metal added to the sensing electrode.

Like example 1, the sensor samples prepared thus were evaluated for sensitivity characteristics to $NO_2$ (100 ppm). FIGS. 17 and 18 show the results of evaluations in case that the electrode under layers were made of zirconia solid electrolytes containing 12-mol % $CeO_2$ or 15-mol % $Sc_2O_3$, respectively.

These results also confirm that the second precious metal of 0.05–5% by weight can be added to the sensing electrode of metal oxide to reduce the rate of change of drift greatly without detriment to the sensitivity characteristics. The results also show that a range of 0.1–3% by weight is preferable, and a range of 0.1–1% by weight is yet preferable.

Example 13

NOx sensors (gas sensing devices) of the present invention having the structure of FIG. 1 were fabricated. In the present example, $Cr_2O_3$ was used as a metal oxide for the sensing electrodes. As the second precious metal, Pt was added to these sensing electrodes with the amount of 0.5% by weight. Further, zirconia solid electrolytes containing the stabilizers shown in Table 9 were added to the sensing electrode with the amount of 10% by weight. Here, no first precious metal was added to the sensing electrode. The electrode under layers 15 were made of three types of zirconia solid electrolytes shown in Table 9. Pt was added to these electrode under layers 15 with the amount of 0.7% by weight. In the present example, the reference electrodes were also made of Pt. The fabrication method of these samples was the same as that of the example 1.

Like example 1, the sensor samples prepared thus were evaluated for sensitivity characteristics to $NO_2$ (100 ppm). Table 9 shows the results. It is found that the addition of zirconia solid electrolyte to the sensing electrode increased the initial sensitivity and improved the electrode stability. Moreover, when the same type of stabilizer was added to the zirconia solid electrolyte of the electrode under layer as the stabilizer of the zirconia solid electrolyte added to the sensing electrode, further improvement was obtained in the stability.

TABLE 9

| Material for electrode under layer | Material for solid electrolyte added to the sensing electrode | Initial sensitivity | Rate of change of drift |
| --- | --- | --- | --- |
| 13 mol % MgO—$ZrO_2$ | — | 85 mV | +24% |
| 13 mol % MgO—$ZrO_2$ | 10 mol % $CeO_2$—$ZrO_2$ | 98 mV | +15% |
| 13 mol % MgO—$ZrO_2$ | 10 mol % MgO—$ZrO_2$ | 100 mV | +11% |
| 13 mol % MgO—$ZrO_2$ | 10 mol % $Sc_2O_3$—$ZrO_2$ | 95 mV | +13% |
| 13 mol % MgO—$ZrO_2$ | 10 mol % $Y_2O_3$—$ZrO_2$ | 102 mV | +14% |

TABLE 9-continued

| Material for electrode under layer | Material for solid electrolyte added to the sensing electrode | Initial sensitivity | Rate of change of drift |
|---|---|---|---|
| 10 mol % CeO$_2$—ZrO$_2$ | — | 90 mV | +21% |
| 10 mol % CeO$_2$—ZrO$_2$ | 10 mol % CeO$_2$—ZrO$_2$ | 102 mV | +10% |
| 10 mol % CeO$_2$—ZrO$_2$ | 10 mol % MgO—ZrO$_2$ | 97 mV | +16% |
| 10 mol % CeO$_2$—ZrO$_2$ | 10 mol % Sc$_2$O$_3$—ZrO$_2$ | 93 mV | +17% |
| 10 mol % CeO$_2$—ZrO$_2$ | 10 mol % Y$_2$O$_3$—ZrO$_2$ | 95 mV | +16% |
| 12 mol % Sc$_2$O$_3$—ZrO$_2$ | — | 89 mV | +24% |
| 12 mol % Sc$_2$O$_3$—ZrO$_2$ | 10 mol % CeO$_2$—ZrO$_2$ | 91 mV | +16% |
| 12 mol % Sc$_2$O$_3$—ZrO$_2$ | 10 mol % MgO—ZrO$_2$ | 95 mV | +14% |
| 12 mol % Sc$_2$O$_3$—ZrO$_2$ | 10 mol % Sc$_2$O$_3$—ZrO$_2$ | 101 mV | +13% |
| 12 mol % Sc$_2$O$_3$—ZrO$_2$ | 10 mol % Y$_2$O$_3$—ZrO$_2$ | 99 mV | +15% |
| 8 mol % Y$_2$O$_3$—ZrO$_2$ | — | 89 mV | +24% |
| 8 mol % Y$_2$O$_3$—ZrO$_2$ | 10 mol % CeO$_2$—ZrO$_2$ | 91 mV | +16% |
| 8 mol % Y$_2$O$_3$—ZrO$_2$ | 10 mol % MgO—ZrO$_2$ | 95 mV | +14% |
| 8 mol % Y$_2$O$_3$—ZrO$_2$ | 10 mol % Sc$_2$O$_3$—ZrO$_2$ | 101 mV | +13% |
| 8 mol % Y$_2$O$_3$—ZrO$_2$ | 10 mol % Y$_2$O$_3$—ZrO$_2$ | 105 mV | +12% |

Example 14

Lamination type NOx sensor devices having the structures shown in FIGS. 4 and 5 were fabricated using the zorconia green sheet with yttria additive of 6% by mole. Electrodes, lead conductors, heaters, and the like were printed on the respective cut green sheets in a screen printer. The individual green sheets were stacked and heated under pressure for mutual bonding. In order to create internal spaces in this green laminate, green sheets that form the spaces are perforated, and then filled with theobromine, which sublimates in the process of degreasing. After degreasing, green laminate was sintered at 1400° C.

In the present example, the sensing electrodes 5 of these sensor devices were made of materials shown in Table 10. The electrode under layer 15 between the sensing electrode 5 and the first solid electrolyte substrate 1 were zirconia solid electrolyte containing 12-mol % ceria as stabilizer and 0.5 wt % Pt as precious metal. The reference electrodes 7 were made of Pt. To check the effects of the electrode under layers, samples having no electrode under layer between the sensing electrode 5 and the first solid electrolyte substrate 1 were also prepared. Moreover, the NOx conversion electrode 8 was made of Pt—Rh (3 wt %) alloy and the NOx conversion counter electrode was made of Pt. Here, no electrode under layer was provided between the NOx conversion electrode 8 and the second solid electrolyte 2 The obtained samples were connected to the control unit. And they were evaluated for sensitivity characteristics while maintaining the temperatures of sensor devices at 600° C. and applying a predetermined voltage to the NOx conversion pump cell. Sensitivity characteristics were evaluated by the same method as the above-mentioned examples were. Here, the total NOx was 100 ppm, or NO of 50 ppm and NO$_2$ of 50 ppm coexisted.

Table 10 shows the results. In both sensor structures, the addition of the first and/or second precious metal to the sensing electrode shows little drop in initial sensitivity and allows a significant improvement in the rate of change of drift.

TABLE 10

| | Material for sensing electrode | | | NOx sensor device having structure of FIG. 2 | | NOx sensor device having structure of FIG. 3 | |
|---|---|---|---|---|---|---|---|
| Material for electrode under layer | Material for metal oxide electrode | Material for first precious metal | Material for second precious metal | Initial sensitivity | Rate of change of drift | Initial sensitivity | Rate of change of drift |
| — | Cr$_2$O$_3$ | — | — | 37 mV | +63% | 35 mV | +71% |
| 12 mol % CeO$_2$—ZrO$_2$ | Cr$_2$O$_3$ | Au-50 wt % | — | 40 mV | +32% | 38 mV | +30% |
| 12 mol % CeO$_2$—ZrO$_2$ | Cr$_2$O$_3$ | — | Pt-0.5 wt % | 38 mV | +23% | 36 mV | +25% |
| 12 mol % CeO$_2$—ZrO$_2$ | Cr$_2$O$_3$ | Au-50 wt % | Pt-0.5 wt % | 42 mV | +18% | 40 mV | +21% |
| 12 mol % CeO$_2$—ZrO$_2$ | NiCr$_2$O$_4$ | — | — | 38 mV | +67% | 33 mV | +76% |
| 12 mol % CeO$_2$—ZrO$_2$ | NiCr$_2$O$_4$ | Au-50 wt % | — | 43 mV | +28% | 41 mV | +32% |
| 12 mol % CeO$_2$—ZrO$_2$ | NiCr$_2$O$_4$ | — | Pt-0.5 wt % | 41 mV | +20% | 42 mV | +26% |
| 12 mol % CeO$_2$—ZrO$_2$ | NiCr$_2$O$_4$ | Au-50 wt % | Pt-0.5 wt % | 40 mV | +15% | 38 mV | +20% |
| 8 mol % Y$_2$O$_3$—ZrO$_2$ | Cr$_2$O$_3$ | — | — | 36 mV | +61% | 34 mV | +73% |
| 8 mol % Y$_2$O$_3$—ZrO$_2$ | Cr$_2$O$_3$ | Au-50 wt % | — | 42 mV | +29% | 39 mV | +25% |
| 8 mol % Y$_2$O$_3$—ZrO$_2$ | Cr$_2$O$_3$ | — | Pt-0.5 wt % | 40 mV | +19% | 39 mV | +22% |
| 8 mol % Y$_2$O$_3$—ZrO$_2$ | Cr$_2$O$_3$ | Au-50 wt % | Pt-0.5 wt % | 39 mV | +16% | 36 mV | +18% |

Example 15

NOx sensors (gas sensing devices) of the present invention having the structure of FIG. 1 were fabricated. In the present example, materials having sensitivity for HC, CO or NH$_3$ was used as the sensing electrodes 5. Further, zirconia solid electrolytes containing the stabilizers shown in Table 11 were added to the sensing electrode with the amount of 10% by weight. The electrode under layers 15 were made of zirconia solid electrolytes containing 15-mol % CeO$_2$ or 15-mol % Sc$_2$O$_3$. As the precious metal, Pt was added to these electrode base layers 15 with the amount of 0.5% by weight. In the present example, the reference electrodes were also made of Pt. The fabrication method of these samples was the same as that of the example 1. To check the effects of the electrode under layers, samples having no electrode under layer were also prepared.

Like example 1, the sensor samples prepared thus were evaluated for sensitivity characteristics to $C_3H_6$ (30 ppm), CO (20 ppm), or $NH_3$ (50 ppm).

Table 11 shows the results. In all cases, the provision of the electrode under layer shows little drop in initial sensitivity and allows a significant improvement in the rate of change of drift.

currents were calculated from the differences between the pump currents after exposing the high temperature accelerate condition and initial pump current to the initial pump current. For the lamination type NOx sensor having the conversion pump cell (oxygen pumping cell), the outputs of each sample with respect to total NOx were evaluated to compare the relative NOx conversion performance. Here, NO gas of 100 ppm was used as NOx. To control the device (oxygen pumping cell or NOx sensor) heating temperature at 600° C., temperature signals of the print type thermocouple

TABLE 11

| Material for solid electrolyte substrate | Sensing electrode part — Material for electrode under layer | Material for sensing electrode | Initial sensitivity $C_3H_6$ | CO | $NH_3$ | Rate of change of drift |
|---|---|---|---|---|---|---|
| 13 mol % MgO—ZrO$_2$ | — | NiCr$_2$O$_4$ | −46 mV | | | +63% |
| 6 mol % Y$_2$O$_3$—ZrO$_2$ | — | NiCr$_2$O$_4$ | −58 mV | | | +51% |
| | | Pt—Rh(5 wt %) | | −41 mV | | +82% |
| | | Cr$_2$O$_3$ | | | −49 mV | +122% |
| 13 mol % MgO—ZrO$_2$ | 10 mol % CeO$_2$—ZrO$_2$ | NiCr$_2$O$_4$ | −42 mV | | | +24% |
| 6 mol % Y$_2$O$_3$—ZrO$_2$ | 10 mol % CeO$_2$—ZrO$_2$ | NiCr$_2$O$_4$ | −50 mV | | | +14% |
| | | Pt—Rh(5 wt %) | | −40 mV | | +31% |
| | | Cr$_2$O$_3$ | | | −42 mV | +42% |
| 13 mol % MgO—ZrO$_2$ | 12 mol % Sc$_2$O$_3$—ZrO$_2$ | NiCr$_2$O$_4$ | −44 mV | | | +20% |
| 6 mol % Y$_2$O$_3$—ZrO$_2$ | 12 mol % Sc$_2$O$_3$—ZrO$_2$ | NiCr$_2$O$_4$ | −53 mV | | | +23% |

Example 16

Oxygen pumping cell having the structure of FIG. 3, and lamination type NOx sensor device having the structure shown in FIG. 4 were fabricated. The solid electrolyte substrate 2 was also made using green sheet obtained from zirconia powder containing 6-mol % $Y_2O_3$. This green sheet was cut into rectangle. Lead conductor of Pt was printed on the green sheet in a screen printer, and then the electrode under layer 9 and first electrode 8 were successively formed in the same method. The electrode under layers 9 were zirconia solid electrolyte containing various stabilizer shown in Table 12 with the amount of 10% by mole. Here, samples having the electrode under layer both without and with the precious metal. For the precious metal, Pt was added to the electrode under layer with the amount of 0.7% by weight. The first electrodes were made of Pt—Rh(3 wt %) alloy. To check the effects of the electrode under layers, samples having no electrode under layer were also prepared. For the second electrode, a conversion counter electrode 10 made of Pt was formed on the another side of the solid electrolyte substrate 2 as the sensing electrode was.

Lamination type NOx sensor device (FIG. 4) having the above-mentioned oxygen pumping cell was fabricated as in the example 14. Here, the sensing electrode was mainly made of $NiCr_2O_4$ and the reference electrode was made of Pt. And no electrode under layer was provided between the sensing electrode 5 and the first solid electrolyte substrate 1.

The obtained samples (oxygen pumping cell) were set in a quartz tube held in an electric furnace and evaluated for oxygen pumping characteristics under an oxygen concentration of 5% by volume. The oxygen pumping characteristics examined were initial pump current and the rate of change of pump current under a predetermined high temperature accelerate condition. The rates of change of pump film embedded in the devices were used to drive the heater for feedback control with the control unit. Incidentally, the applying voltage to the oxygen pumping cell or NOx conversion cell of NOx sensor was set at 0.5 V.

Table 12 shows the results. In case that no precious metal was added to the electrode under layer, it is found that the samples having zirconia electrode under layers containing a stabilizer other than yttria ($Y_2O_3$), especially, magnesia (MgO), ceria ($CeO_2$), or scandia ($Sc_2O_3$), suppressed the rate of the change of the pump current. The sample having a zirconia electrode under layer containing $Y_2O_3$ shows considerable high initial pump current. However, it is found that as compared to the samples containing a stabilizer other than $Y_2O_3$, the drift (rate of change of pump current) suppressing effect of this sample was clearly low.

In each sample, adding Pt to the zirconia electrode under layer increased the initial pump current of the oxygen pumping cell. Moreover, the rate of the change of drift was further reduced. Here, Pt can be added to the zirconia under layer containing $Y_2O_3$ to significantly improve the stability of the pumping cell. In case that precious metal (Pt) was added to the zirconia electrode under layer, the results show that $Y_2O_3$, MgO, $CeO_2$, or $Sc_2O_3$ is preferably used as a stabilizer of zirconia solid electrolyte. Moreover, it is clear that the mixed potential type NOx sensor having the oxygen pumping cell of the present invention as a NOx conversion pump cell offers increase in the output of sensor while converting NOx into $NO_2$ and thereby detecting the total NOx concentration. The results confirm that in each sample, Pt can be added to further increase the output of NOx sensor.

TABLE 12

| Material for electrode under layer | Oxygen pump cell having structure of FIG. 3 | | | | Output of NOx sensor having structure of FIG. 4 | |
|---|---|---|---|---|---|---|
| | Ininial pump current | | Rate of change of pump current | | | |
| | no precious metal | Pt (0.7 wt %) | no precious metal | Pt (0.7 wt %) | no precious metal | Pt (0.7 wt %) |
| — | 505 μA | — | −75% | — | 20 mV | — |
| $Y_2O_3$(10 mol %)—$ZrO_2$ | 543 μA | 620 μA | −55% | −19% | 36 mV | 53 mV |
| CaO(10 mol %)—$ZrO_2$ | 480 μA | 498 μA | −34% | −25% | 33 mV | 41 mV |
| MgO(10 mol %)—$ZrO_2$ | 510 μA | 610 μA | −25% | −20% | 38 mV | 55 mV |
| $CeO_2$(10 mol %)—$ZrO_2$ | 509 μA | 635 μA | −21% | −18% | 39 mV | 58 mV |
| $Sc_2O_3$(10 mol %)—$ZrO_2$ | 550 μA | 658 μA | −23% | −19% | 40 mV | 59 mV |
| $ThO_2$(10 mol %)—$ZrO_2$ | 466 μA | 495 μA | −38% | −27% | 28 mV | 33 mV |
| $Yb_2O_3$(10 mol %)—$ZrO_2$ | 425 μA | 453 μA | −36% | −28% | 24 mV | 30 mV |

Example 17

Oxygen pumping cells having the structure shown in FIG. 3 were fabricated as in the example 16. The electrode under layers 9 were zirconia solid electrolyte containing MgO, $CeO_2$, or $Sc_2O_3$ as stabilizer with the amount of 8% by mole. To examine the influence of the added amount of $Y_2O_3$, $Y_2O_3$ was added to the zirconia solid electrolyte of the electrode under layer with different amount.

Moreover, for the purpose of comparison, samples added no stabilizer other than $Y_2O_3$ was likewise fabricated. Here, no precious metal was added to the electrode under layer. The obtained samples were evaluated for oxygen pump performance and high temperature accelerating degradation as in the example 16.

Figure 19:
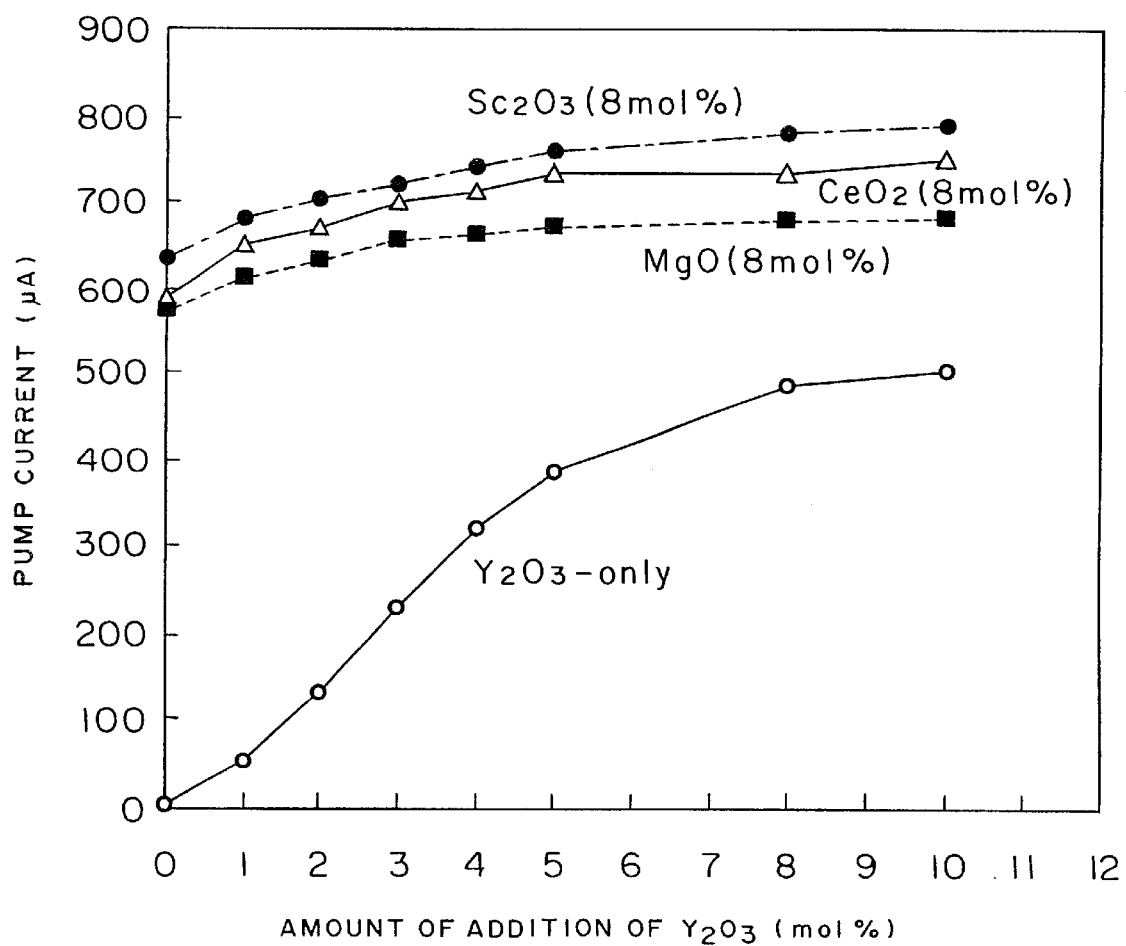
FIG. 19 shows pump current as a function of amount of addition of $Y_2NO_3$.
Figure 20:
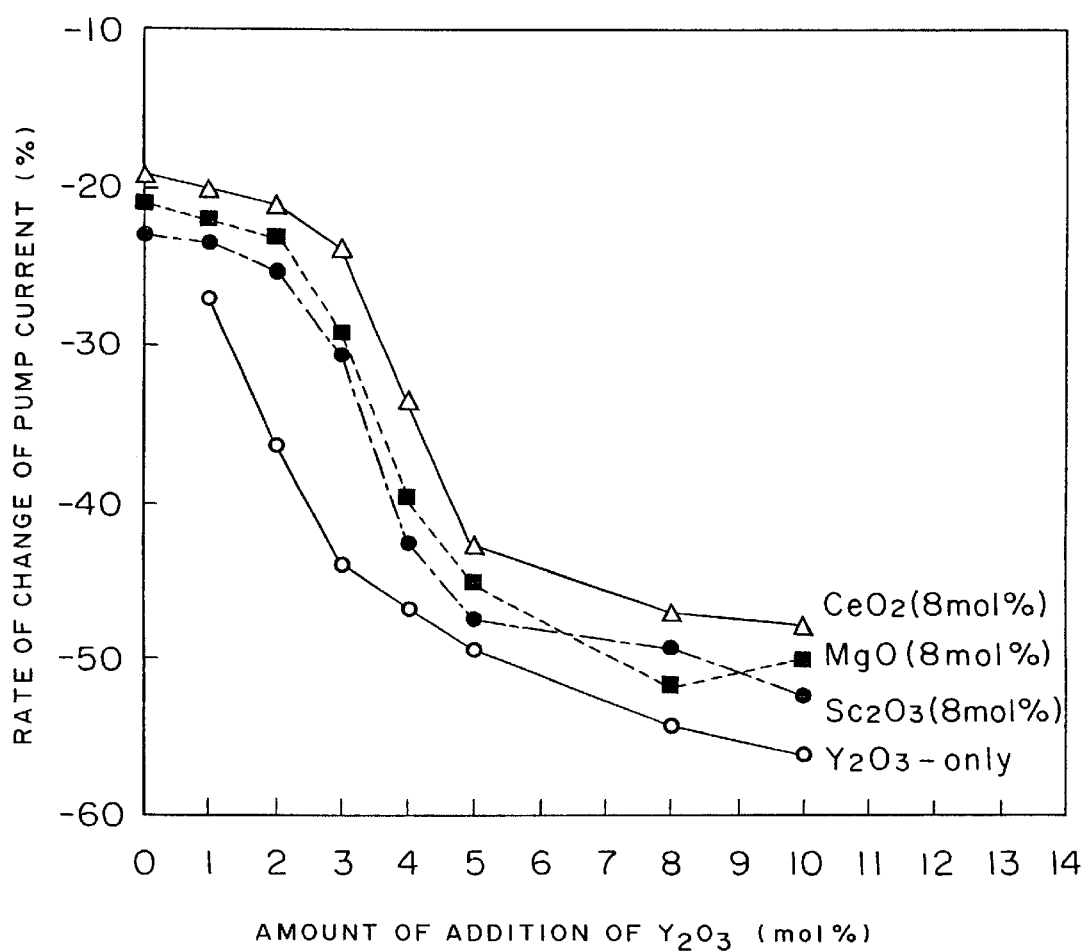
FIG. 20 shows rate of change of pump current as a function of amount of addition of $Y_2NO_3$.

FIGS. 19 and 20 show the results of evaluation as to initial pump current and the change rate of pump current while changing the added amount of $Y_2O_3$, respectively. FIG. 19 confirms that a predetermined amount (8% by mole) of the stabilizer other than $Y_2O_3$, such as MgO, $CeO_2$, $Sc_2O_3$ and the like, can be added to the zirconia solid electrolyte of electrode under layer (zirconia electrode under layer) to increase the initial pump currents and to obtain superior oxygen pump performance without the addition of $Y_2O_3$. Moreover, it is found that the initial pump currents further increase with an increasing added amount of $Y_2O_3$ in all cases.

On the other hand, FIG. 20 shows that in each case, the rate of change of pump current increased with an increasing added amount of $Y_2O_3$ to reduce the stability of the oxygen pumping cell. In term of the stability of the oxygen pumping cell, it is desirable that $Y_2O_3$ is not added to the zirconia solid electrolyte of the electrode under layer. $Y_2O_3$ of not more than 3% by mole, preferably not more than 2% by mole, yet preferably not more than 1% by mole can be added not to suffer from a practical problem. On the contrary, $Y_2O_3$ of this range can be added to reduce the amount of non-yttria stabilizer while maintaining the pump performance at a predetermined level. Therefore, $Y_2O_3$ is desirably used together in terms of costs.

Example 18

Oxygen pumping cell having the structure of FIG. 3, and lamination type NOx sensor devices having the structures shown in FIGS. 4 and 5 were fabricated as in example 16. The electrode under layers 9 were made of zirconia solid electrolyte containing ceria with the amount of 12% by mole. Moreover, various precious metals or metal alloys shown in Table 13 with the amount of 0.5% by weight were added to the electrode under layer. The first electrodes were made of Pt—Rh(5 wt %) alloy. To check the effects of the precious metal or metal alloy added to the electrode under layer, sample not containing both precious metal and metal alloy in the electrode under layer was also prepared. For the second electrode, the conversion counter electrode made of Pt was formed in the air duct 12.

The sensing electrodes of lamination type NOx sensor devices were mainly made of $NiCr_2O_4$ and the reference electrodes were made of Pt. Here, no electrode under layer was provided between the sensing electrode 5 and the first solid electrolyte substrate 1. The obtained samples of oxygen pumping cell and the lamination type NOx sensor were evaluated as in example 16.

Table 13 shows the results. It is found from the results that the electrode under layer made of ceria-added zirconia solid electrolyte containing a precious metal and metal alloy increased the pump current of the oxygen pumping cell. Moreover, it is clear that the mixed potential type NOx sensor having the oxygen pumping cell of the present example as a NOx conversion pump cell offers increase in the sensor output while converting NOx into $NO_2$ and thereby detecting the total NOx concentration. Here, it is found that precious metal or metal alloy active to NOx, such as Ir, Au, Rh, Pt—Rh ally, Ir—Rh alloy and Ir—Ru alloy can be added to the zirconia electrode under layer to increase the output of NOx sensor greatly.

TABLE 13

| Material for precious metal added to zirconia said electrolyte of electrode under layer | Pump current of oxygen pump cell Ininitial pump current | Output of Nox sensor having structure of FIG. 4 | Output of NOx sensor having structure of FIG. 5 |
|---|---|---|---|
| — | 560 μA | 38 mV | 32 mV |
| Pt-0.5 wt % | 625 μA | 42 mV | 37 mV |
| Pd-0.5 wt % | 636 μA | 45 mV | 36 mV |
| Ir-0.5 wt % | 612 μA | 51 mV | 43 mV |
| Au-0.5 wt % | 607 μA | 49 mV | 41 mV |
| Ru-0.5 wt % | 634 μA | 42 mV | 38 mV |
| Rh-0.5 wt % | 618 μA | 49 mV | 44 mV |
| (Pt-3 wt % Rh)-0.5 wt % | 615 μA | 56 mV | 49 mV |
| (Ir-5 wt % Rh)-0.5 wt % | 610 μA | 54 mV | 46 mV |
| (Pt-5 wt % Ru)-0.5 wt % | 653 μA | 52 mV | 44 mV |

Example 19

Lamination type NOx sensor devices having the structure shown in FIG. 4 were fabricated as in example 16. The electrode under layers 9 were made of zirconia solid electrolyte containing ceria with the amount of 12% by mole. As the precious metal or metal alloy, Pt, Pd, Rh, Ir, Pt-3 wt % Rh and Ir-5 wt % Rh were added to the electrode under layers with different amounts in the range of 0–7% by weight. The first electrodes were made of Pt—Rh(5 wt %) alloy. The obtained samples were evaluated as in example 16.

Table 14 shows the results. These results confirms that in each sample, the precious metal and metal alloy of 0.05–5% by weight can be added to increase the output of NOx sensor clearly. The results also show that a range of 0.1–2% by weight is preferable. Moreover, it is found that precious metal or metal alloy active to NOx, such as Rh, Ir, Pt—Rh alloy and Ir—Rh alloy can be added to the zirconia electrode base layer to increase the output of NOx sensor greatly.

TABLE 14

| Amount of addition | Precious metal added to electrode under layer | | | | | |
|---|---|---|---|---|---|---|
| | Pt | Pd | Rh | Ir | Pt-3 wt % Rh | Ir-5 wt % Rh |
| 0 wt % | | | | 37 mV | | |
| 0.01 wt % | 37 mV | 34 mV | 38 mV | 37 mV | 38 mV | 35 mV |
| 0.05 wt % | 39 mV | 38 mV | 41 mV | 38 mV | 42 mV | 40 mV |
| 0.1 wt % | 41 mV | 40 mV | 46 mV | 47 mV | 55 mV | 49 mV |
| 0.5 wt % | 43 mV | 44 mV | 52 mV | 53 mV | 57 mV | 55 mV |
| 1 wt % | 42 mV | 44 mV | 51 mV | 50 mV | 56 mV | 54 mV |
| 2 wt % | 41 mV | 42 mV | 49 mV | 49 mV | 52 mV | 50 mV |
| 3 wt % | 40 mV | 38 mV | 44 mV | 45 mV | 49 mV | 47 mV |
| 5 wt % | 38 mV | 36 mV | 40 mV | 39 mV | 42 mV | 41 mV |
| 7 wt % | 25 mV | 24 mV | 30 mV | 26 mV | 26 mV | 30 mV |

Example 20

Oxygen pumping cell devices having the structure shown in FIG. 3 and lamination type NOx sensor devices having the structures shown in FIGS. 4 and 5 were fabricated as in example 16. The electrode under layers 9 were made of zirconia solid electrolyte containing ceria with the amount of 10% by mole. Here, a voidage (porosity) of the electrode under layer was controlled by adjusting the particle size of the raw material powder, the viscosity of the paste, or the like.

The obtained samples were evaluated as in example 16. Table 15 shows the results. Incidentally, the voidage shown in Table 15 was obtained from the measurement of the electrode under layer embedded in the oxygen pumping cell.

These results confirms that voidage in the range of 4.8–37% by volume offers increasing effect both in the pump current of the oxygen pumping cell and the output of the NOx sensor greatly.

TABLE 15

| Voidage of electrode under layer | Pump current of oxygen pump cell | Output of NOx sensor having structure of FIG. 4 | Output of NOx sensor having structure of FIG. 5 |
|---|---|---|---|
| 1.9% | 610 μA | 44 mV | 38 mV |
| 4.8% | 628 μA | 46 mV | 39 mV |
| 9.8% | 641 μA | 52 mV | 44 mV |

TABLE 15-continued

| Voidage of electrode under layer | Pump current of oxygen pump cell | Output of NOx sensor having structure of FIG. 4 | Output of NOx sensor having structure of FIG. 5 |
|---|---|---|---|
| 16.7% | 662 μA | 55 mV | 49 mV |
| 28.6% | 647 μA | 48 mV | 42 mV |
| 37% | 615 μA | 46 mV | 42 mV |
| 46.1% | 586 μA | 44 mV | 41 mV |

Example 21

Oxygen pumping cell devices having the structure shown in FIG. 3 and lamination type NOx sensor devices having the structures shown in FIGS. 4 and 5 were fabricated as in example 16. The electrode under layers 9 were made of zirconia solid electrolyte containing ceria with the amount of 10% by mole. Here, a thickness of the electrode under layer was controlled by changing the times of screen printing.

The obtained samples were evaluated as in example 16. Table 16 shows the results. Incidentally, the average thickness shown in Table 15 was obtained from the measurement of the electrode under layer embedded in the oxygen pumping cell. These results confirms that thickness in the range of 2.9–29.6 μm offers increasing effect both in the pump current of the oxygen pumping cell and the output of the NOx sensor greatly.

TABLE 16

| Thickness of electrode under layer | Pump current of oxygen pump cell | Output of NOx sensor having structure of FIG. 4 | Output of NOx sensor having structure of FIG. 5 |
|---|---|---|---|
| 1.9 μm | 568 μA | 44 mV | 36 mV |
| 2.9 μm | 596 μA | 46 mV | 39 mV |
| 6.1 μm | 625 μA | 53 mV | 44 mV |
| 13.2 μm | 643 μA | 52 mV | 47 mV |
| 20.7 μm | 688 μA | 48 mV | 39 mV |
| 29.6 μm | 640 μA | 45 mV | 40 mV |
| 36.5 μm | 630 μA | 39 mV | 33 mV |

Example 22

Oxygen pumping cell devices having the structure shown in FIG. 3 and lamination type NOx sensor devices having the structures shown in FIGS. 4 and 5 were fabricated as in example 16. As the stabilizer, ceria was added to the zirconia electrode under layer 9 with different amounts shown in Table 17. Here, a thickness of the electrode under layer was set to 10 μm.

The obtained samples were evaluated as in example 16. Table 17 shows the results. These results confirms that ceria (stabilizer) of 3.0–30.5% by mole can be added to increase both the pump current of the oxygen pump cell and the output of NOx sensor greatly. The results also show that a range of 5–20% by mole is preferable

TABLE 17

| Amount of stabilizer added to zirconia electrode under layer | Pump current of oxygen pump cell | Output of NOx sensor having structure of FIG. 4 | Output of NOx sensor having structure of FIG. 5 |
|---|---|---|---|
| 1.5 mol % | 123 µA | 13 mV | 11 mV |
| 3.0 mol % | 380 µA | 41 mV | 32 mV |
| 5.1 mol % | 521 µA | 45 mV | 88 mV |
| 7.5 mol % | 594 µA | 50 mV | 43 mV |
| 10.1 mol % | 647 µA | 53 mV | 47 mV |
| 12.6 mol % | 656 µA | 51 mV | 42 mV |
| 15.2 mol % | 649 µA | 46 mV | 33 mV |
| 20.2 mol % | 638 µA | 39 mV | 31 mV |
| 30.5 mol % | 515 µA | 32 mV | 24 mV |
| 40.5 mol % | 420 µA | 19 mV | 16 mV |

Example 23

Oxygen pumping cell devices having the structure shown in FIG. 3 were fabricated as in example 16. Here, zirconia solid electrolyte powder was also added to the first electrode 8. The stabilizer shown in Table 18 was added to the zirconia electrode under layer 9 and the zirconia solid electrolyte added to the first electrode, respectively. The amount of zirconia solid electrolyte added to the first electrode was set to 10% by weight and the thickness of the electrode under layer was set to 10 µm.

The obtained samples were evaluated as in example 16. Table 18 shows the results. It is found that the addition of zirconia solid electrolyte to the first electrode improved both the oxygen pump performance and stability greatly. Moreover, when the same type of stabilizer was added to the zirconia solid electrolyte of the electrode under layer as the stabilizer of the zirconia solid electrolyte added to the first electrode, most superior oxygen pump performance and stability could be obtained.

TABLE 18

| Material for stabilizer added to zirconia electrode under layer | Stabilizer of zirconia solid electrolyte added to first electrode | Initial pump current | | Rate of change of pump current | |
|---|---|---|---|---|---|
| | | no precious metal | Pt (0.7 wt %) | no precious metal | Pt (0.7 wt %) |
| MgO (10 mol %) | Y₂O₃ (10 mol %) | 590 µA | 642 µA | −23% | −20% |
| MgO (10 mol %) | CeO₂ (10 mol %) | 612 µA | 651 µA | −18% | −16% |
| MgO (10 mol %) | MgO (10 mol %) | 620 µA | 660 µA | −12% | −12% |
| MgO (10 mol %) | Sc₂O₃ (10 mol %) | 570 µA | 638 µA | −21% | −19% |
| CeO₂ (10 mol %) | Y₂O₃ (10 mol %) | 611 µA | 649 µA | −19% | −17% |
| CeO₂ (10 mol %) | CeO₂ (10 mol %) | 653 µA | 685 µA | −10% | −10% |
| CeO₂ (10 mol %) | MgO (10 mol %) | 598 µA | 668 µA | −16% | −15% |
| CeO₂ (10 mol %) | Sc₂O₃ (10 mol %) | 606 µA | 670 µA | −13% | −13% |
| Sc₂O₃ (10 mol %) | Y₂O₃ (10 mol %) | 574 µA | 675 µA | −21% | −20% |
| Sc₂O₃ (10 mol %) | CeO₂ (10 mol %) | 624 µA | 686 µA | −19% | −17% |
| Sc₂O₃ (10 mol %) | MgO (10 mol %) | 640 µA | 674 µA | −17% | −15% |
| Sc₂O₃ (10 mol %) | Sc₂O₃ (10 mol %) | 654 µA | 693 µA | −11% | −10% |

Example 24

Lamination type NOx sensor devices having the structure shown in FIG. 7 were fabricated as in example 16. Here, two types of sample (A: the electrode under layers are formed under the NOx conversion electrode 8 and the gas treatment electrode 19, B: electrode under layers are formed under the NOx conversion electrode 8, the gas treatment electrode 19, and the sensing electrode 5) were prepared. The electrode under layers were made of 8 mol % yttria added zirconia containing Pt with the amount of 0.6% by weight. The thickness of the electrode under layer was set to 10 µm. For comparison, sample having no electrode under layer was also prepared. The NOx conversion electrode was made of Pt—Rh(5 wt %) alloy and the gas treatment electrode was made of Pt—Pd(5 wt %) alloy.

The obtained samples were evaluated as in example 16. Here, the output of NOx sensor with respect to NO was measured by using nitrogen-based gas containing 100-ppm NO. Further, to check the performance of reducing the interference gas, the output of NOx sensor was also measured by using nitrogen-based gas containing both 100-ppm NO and 5000-ppm $C_3H_6$. Incidentally, the applying voltage to the gas treatment cell (19, 10) was set at 0.5V. Table 19 shows the results. It is found that the provision of electrode under layer under the NOx conversion electrode and the gas treatment electrode improved the reducing gas removal efficiency. Moreover, the electrode under layer can be formed under the sensing electrode to further increase the output of the NOx sensor.

TABLE 19

| | Output of NOx sensor | | |
|---|---|---|---|
| Measured gas (N₂ base) | No under layer | A* | B** |
| 100 ppm-NO | 38 mV | 43 mV | 49 mV |
| 100 ppm-NO + 5000 ppm C₃H₆ | 28 mV | 42 mV | 47 mV |

A*: Under layers are formed under the NOx conversion electrode 8 and the gas treatment electrode 19.
B**: Under layers are formed under the NOx conversion electrode 8, the gas treatmentelectrode 19, and the sensing electrode 5.

What is claimed is:

1. A mixed potential type gas sensing device comprising: an oxygen-ion-conductive solid electrolyte substrate; a sensing electrode active to a gas to be detected and oxygen, arranged on one side of said solid electrolyte substrate; and a reference electrode active to at least oxygen, fixed onto the other side of said solid electrolyte substrate, the gas sensing device further comprising an electrode under layer made of an oxygen-ion-conductive solid electrolyte between said sensing electrode and said solid electrolyte substrate, wherein said electrode under layer contains at least one material selected from the group consisting of magnesia, ceria and scandia as a stabilizer.

2. A gas sensing device comprising: an oxygen-ion-conductive solid electrolyte substrate; a sensing electrode active to a gas to be detected and oxygen, arranged on one side of said solid electrolyte substrate; and a reference electrode active to oxygen and inactive to said gas to be detected, fixed onto the same side of said solid electrolyte substrate, the gas sensing device further comprising an electrode under layer made of an oxygen-ion-conductive solid electrolyte between said sensing electrode and said solid electrolyte substrate, wherein said electrode under layer contains at least one material selected from the group consisting of magnesia, ceria and scandia as a stabilizer.

3. The gas sensing device according to claim 1 or 2, wherein said electrode under layer is yttria-free or contains yttria of not more than 3% by mole.

4. A gas sensing device for detecting NOx comprising: an oxygen-ion-conductive solid electrolyte substrate; a sensing electrode active to a gas to be detected and oxygen, arranged on one side of said solid electrolyte substrate; and a reference electrode active to at least oxygen, fixed onto the other side of said solid electrolyte substrate, the gas sensing device further comprising an electrode under layer made of an oxygen-ion-conductive solid electrolyte between said sensing electrode and said solid electrolyte substrate, wherein said electrode under layer contains at least one precious metal selected from the group consisting of Au, Ir, and Rh.

5. A gas sensing device for detecting NOx comprising: an oxygen-ion-conductive solid electrolyte substrate; a sensing electrode active to a gas to be detected and oxygen, arranged on one side of said solid electrolyte substrate; and a reference electrode active to oxygen and inactive to said gas to be detected, fixed onto the same side of said solid electrolyte substrate, the gas sensing device further comprising an electrode under layer made of an oxygen-ion-conductive solid electrolyte between said sensing electrode and said solid electrolyte substrate, wherein said electrode under layer contains at least one precious metal selected from the group consisting of Au, Ir, and Rh.

6. A gas sensing device for detecting NOx comprising: an oxygen-ion-conductive solid electrolyte substrate; a sensing electrode active to a gas to be detected and oxygen, arranged on one side of said solid electrolyte substrate; and a reference electrode active to at least oxygen, fixed onto the other side of said solid electrolyte substrate, the gas sensing device further comprising an electrode under layer made of an oxygen-ion-conductive solid electrolyte between said sensing electrode and said solid electrolyte substrate, wherein said electrode under layer contains at least one precious metal selected from the group consisting of Pt, Pd, and Ru and the content of said precious metal falls within a range of 0.05–4% by weight with respect to the total amount of said electrode under layer.

7. A gas sensing device for detecting NOx comprising: an oxygen-ion-conductive solid electrolyte substrate; a sensing electrode active to a gas to be detected and oxygen, arranged on one side of said solid electrolyte substrate; and a reference electrode active to oxygen and inactive to said gas to be detected, fixed onto the same side of said solid electrolyte substrate, the gas sensing device further comprising an electrode under layer made of an oxygen-ion-conductive solid electrolyte between said sensing electrode and said solid electrolyte substrate, wherein said electrode under layer contains at least one precious metal selected from the group consisting of Pt, Pd, and Ru and the content of said precious metal falls within a range of 0.05–4% by weight with respect to the total amount of said electrode under layer.

8. An oxygen pumping cell comprising:

an oxygen-ion-conductive solid electrolyte substrate;

a first electrode active to at least a gas to be processed and oxygen, arranged on said solid electrolyte substrate;

a second electrode active to at least oxygen, arranged on said solid electrolyte substrate; and means for applying a predetermined voltage between said electrodes, the oxygen pumping cell further comprising an electrode under layer made of an oxygen-ion-conductive solid electrolyte at least between said first electrode and said solid electrolyte substrate, wherein said electrode under layer contains at least one material selected from the group consisting of magnesia, ceria and scandia as a stabilizer.

9. An oxygen pumping cell comprising:

an oxygen-ion-conductive solid electrolyte substrate;

a first electrode active to at least a gas to be processed and oxygen, arranged on said solid electrolyte substrate;

a second electrode active to at least oxygen, arranged on said solid electrolyte substrate; and means for applying a predetermined voltage between said electrodes, the oxygen pumping cell further comprising an electrode under layer made of an oxygen-ion-conductive solid electrolyte at least between said first electrode and said solid electrolyte substrate, wherein said electrode under layer contains at least one precious metal selected from the group consisting of Pt, Pd, Ir, Au, Ru and Rh and the content of said precious metal falls within a range of 0.05–5% by weight with respect to the total amount of said electrode under layer.

* * * * *